United States Patent
Takahashi et al.

(10) Patent No.: US 11,000,180 B2
(45) Date of Patent: May 11, 2021

(54) FLEXIBLE TUBE INSERTION APPARATUS

(71) Applicant: OLYMPUS CORPORATION, Tokyo (JP)

(72) Inventors: Takeshi Takahashi, Hachioji (JP); Shuji Nakamura, Akishima (JP)

(73) Assignee: OLYMPUS CORPORATION, Tokyo (JP)

( * ) Notice: Subject to any disclaimer, the term of this patent is extended or adjusted under 35 U.S.C. 154(b) by 371 days.

(21) Appl. No.: 15/977,368

(22) Filed: May 11, 2018

(65) Prior Publication Data

US 2018/0263467 A1   Sep. 20, 2018

Related U.S. Application Data

(63) Continuation of application No. PCT/JP2015/086396, filed on Dec. 25, 2015.

(51) Int. Cl.
| | |
|---|---|
| *A61B 1/00* | (2006.01) |
| *A61B 1/005* | (2006.01) |
| *A61B 1/01* | (2006.01) |
| *A61B 1/273* | (2006.01) |

(52) U.S. Cl.
CPC ...... *A61B 1/00078* (2013.01); *A61B 1/00006* (2013.01); *A61B 1/00045* (2013.01); *A61B 1/0053* (2013.01); *A61B 1/0055* (2013.01); *A61B 1/00133* (2013.01); *A61B 1/00147* (2013.01); *A61B 1/01* (2013.01); *A61B 1/00165* (2013.01); *A61B 1/273* (2013.01)

(58) Field of Classification Search
None
See application file for complete search history.

(56) References Cited

U.S. PATENT DOCUMENTS 4,601,283 A * 7/1986 Chikama .................. A61B 1/31
                                                219/201
4,753,223 A * 6/1988 Bremer ................. A61B 1/0058
                                                600/140

(Continued)

FOREIGN PATENT DOCUMENTS

| | | |
|---|---|---|
| EP | 3 275 357 A1 | 1/2018 |
| JP | S61-37931 B2 | 8/1986 |

(Continued)

OTHER PUBLICATIONS

Chinese Office Action dated Sep. 3, 2019 in Chinese Patent Application No. 201580085542.6.

(Continued)

*Primary Examiner* — Timothy J Neal
(74) *Attorney, Agent, or Firm* — Scully, Scott, Murphy & Presser, P.C.

(57) ABSTRACT

A flexible tube insertion apparatus includes an insertion section, one or more stiffness variable portion, and a detection unit. The flexible tube insertion apparatus includes a bending information calculator, a main determiner, and a controller that performs control to increase a stiffness of the stiffness variable portion provided in a segment located in a bent part, when the main determiner determines that the bent part is present and the segment provided in the stiffness variable portion is located in the bent part.

8 Claims, 16 Drawing Sheets

(56) References Cited

U.S. PATENT DOCUMENTS

| | | | | |
|---|---|---|---|---|
| 4,846,573 A | * | 7/1989 | Taylor | A61B 1/0053 356/241.4 |
| 5,188,111 A | * | 2/1993 | Yates | G01R 33/285 600/434 |
| 5,482,029 A | * | 1/1996 | Sekiguchi | A61B 1/00039 600/109 |
| 6,432,041 B1 | | 8/2002 | Taniguchi et al. | |
| 2002/0062062 A1 | * | 5/2002 | Belson | A61B 1/0053 600/146 |
| 2007/0038023 A1 | * | 2/2007 | Uchimura | A61B 1/00078 600/109 |
| 2007/0270649 A1 | * | 11/2007 | Long | A61B 1/0053 600/144 |
| 2009/0171151 A1 | * | 7/2009 | Choset | A61B 1/31 600/114 |

FOREIGN PATENT DOCUMENTS

| | | |
|---|---|---|
| JP | H6-181882 A | 7/1994 |
| JP | 2000-166860 A | 6/2000 |
| JP | 4009519 B2 | 11/2007 |
| JP | 5574415 B2 | 8/2014 |

OTHER PUBLICATIONS

Extended Supplementary European Search Report dated Jul. 25, 2019 in European Patent Application No. 15 91 1422.2.

English translation of International Preliminary Report on Patentability dated Jul. 5, 2018 together with the Written Opinion received in related International Application No. PCT/JP2015/086396.

International Search Report dated Mar. 29, 2016 issued in PCT/JP2015/086396.

* cited by examiner

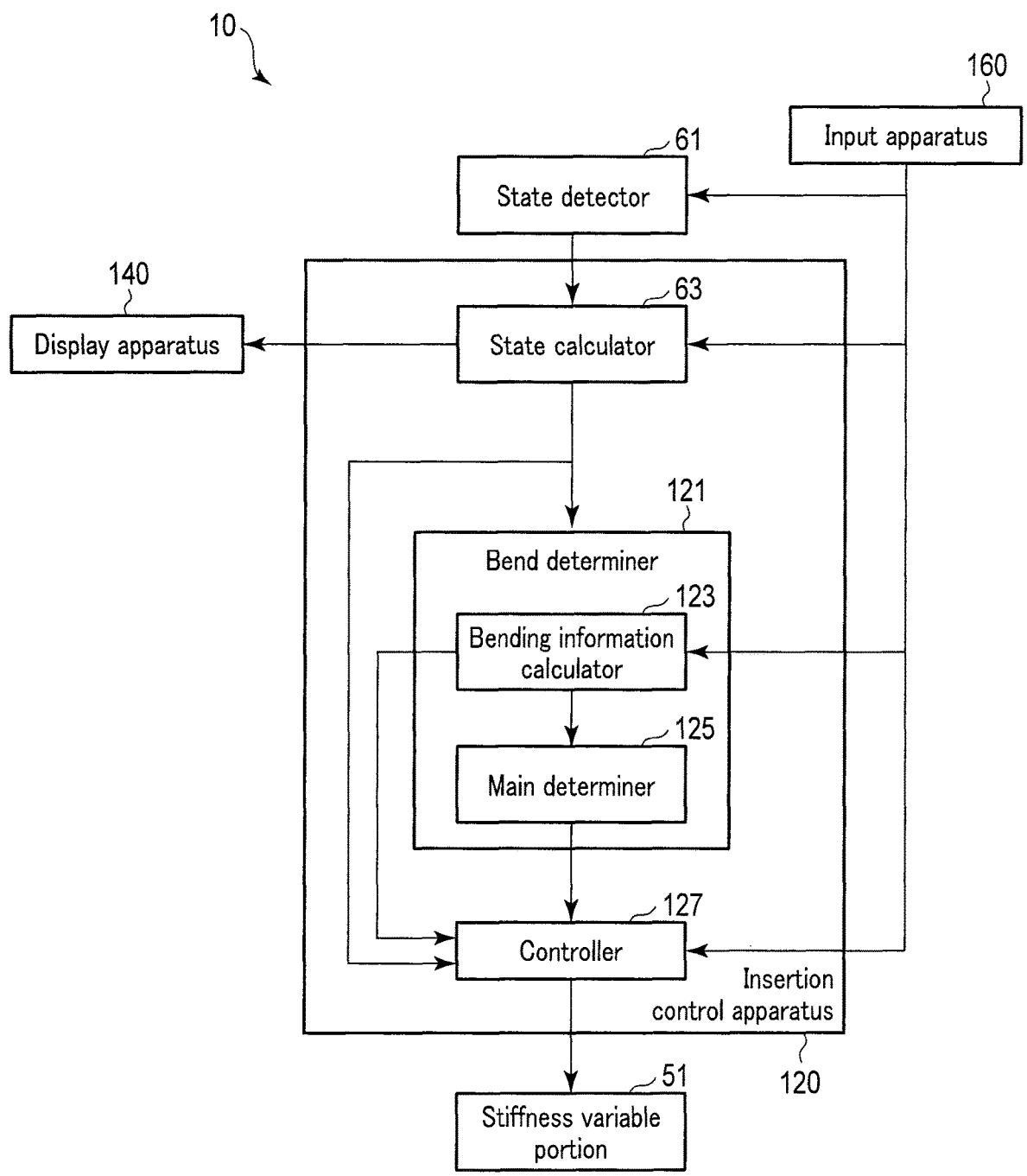
F I G. 2

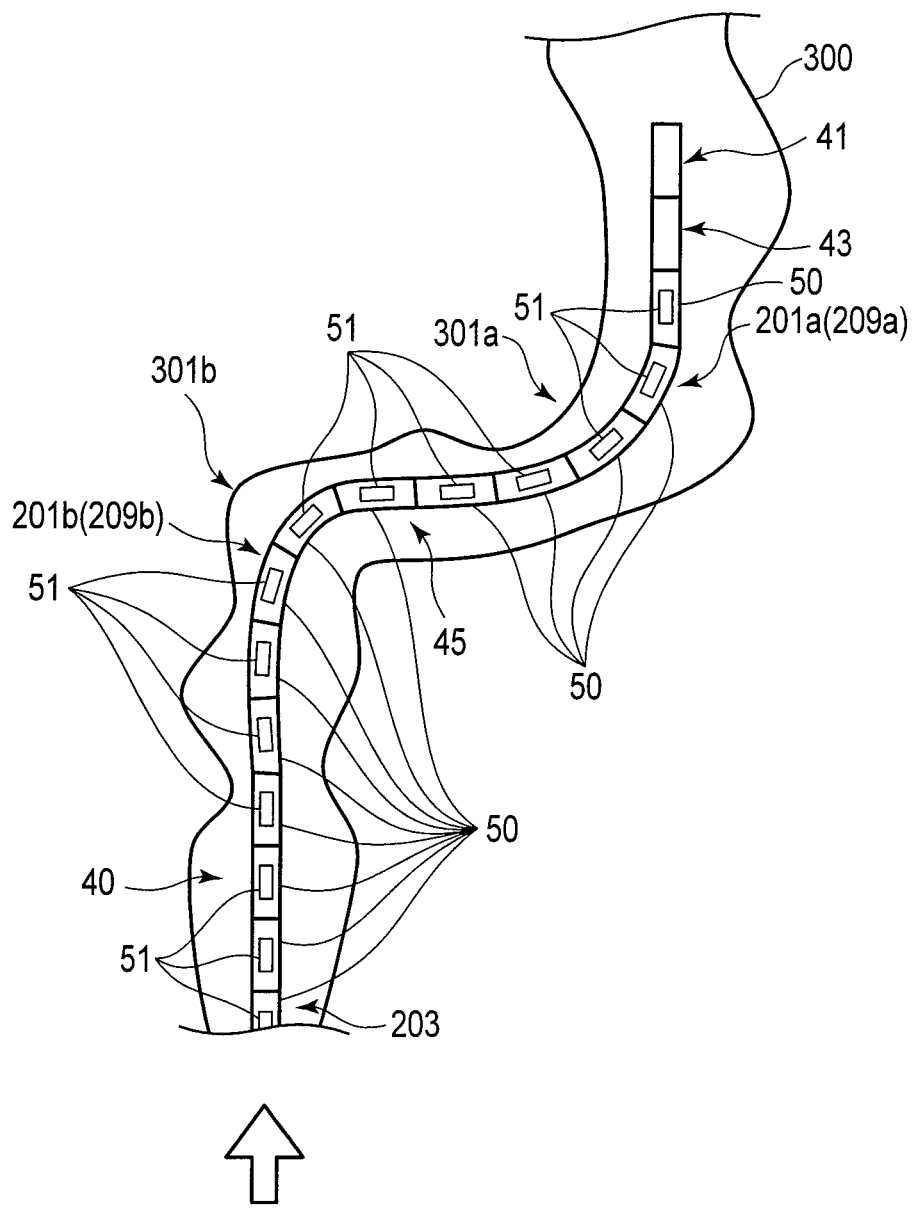
F I G. 4B

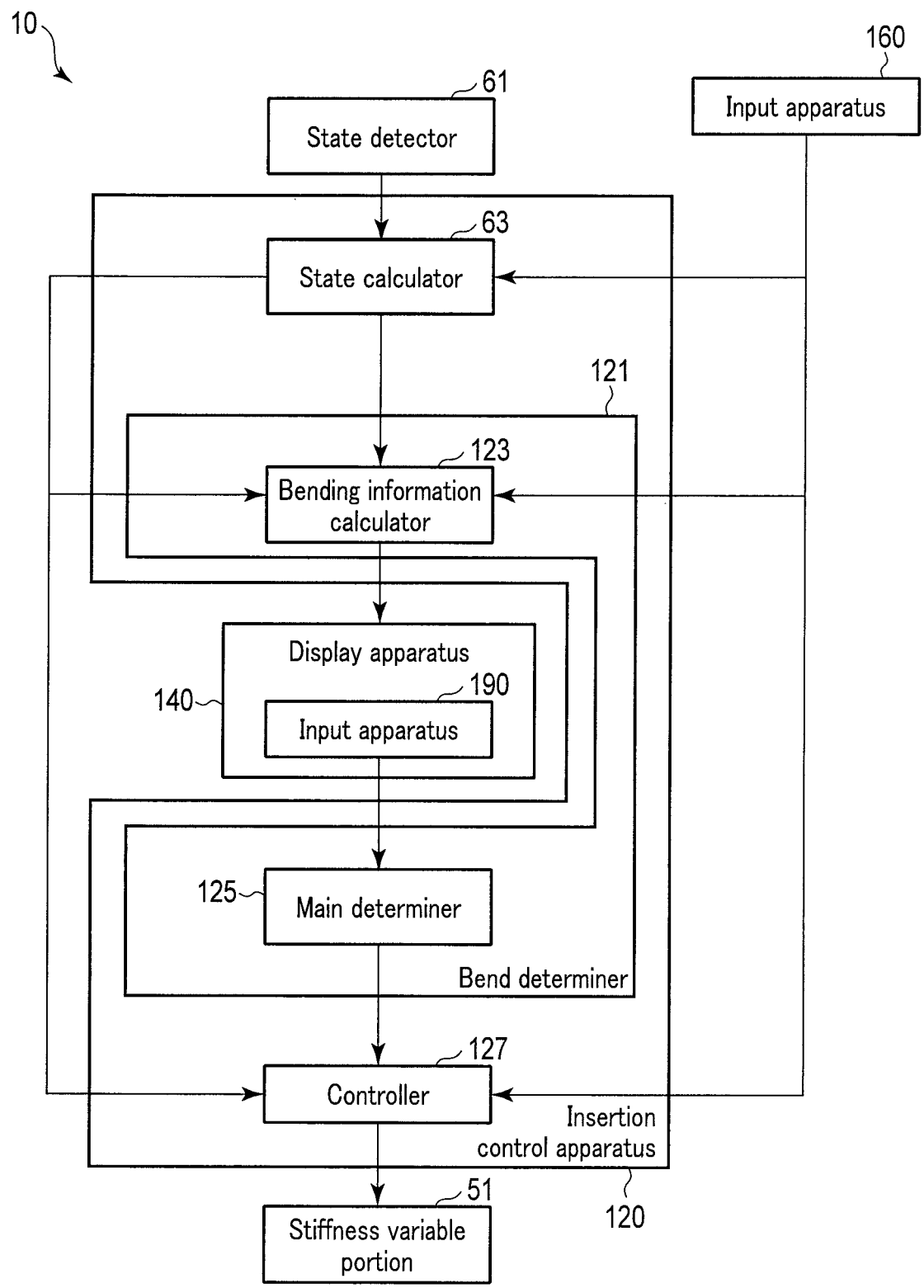
F I G. 6A

FLEXIBLE TUBE INSERTION APPARATUS

CROSS-REFERENCE TO RELATED APPLICATIONS

This application is a Continuation Application of PCT Application No. PCT/JP2015/086396, filed Dec. 25, 2015, the entire contents of all of which are incorporated herein by references.

BACKGROUND OF THE INVENTION

1. Field of the Invention

The present invention relates to a flexible tube insertion apparatus.

2. Description of the Related Art

When a flexible, elongated insertion section is pushed forward into the inside of the large intestine (tube (tube portion)), the operator pushes the insertion section forward while gripping a proximal end portion of the insertion section exposed to the outside from the anus. Normally, the sigmoid colon, the transverse colon, and the like are not fixed within the abdomen, and are easily moved inside the abdomen. In an intestinal tract that is easily bent and moved by a push operation of the insertion section, the hand side force that pushes the insertion section forward may not be easily transmitted to a distal end portion of the insertion section. This is because the insertion section may be flexed in a direction different from the direction in which the insertion section is pushed forward, causing buckling that bends the insertion section in an unintended direction, for example. Such buckling prevents the hand side force from being easily transmitted to the distal end of the insertion section, and the distal end portion of the insertion section is prevented from being inserted toward (advancing toward) a deep portion, namely, the insertability is reduced. The deep portion refers to a position ahead of the current position in the insertion direction.

To allow the hand side force to be easily transmitted to the distal end side of the insertion section, the operator has been using various procedures to make a buckling part of the insertion section in which buckling occurs substantially straight. As an example of such procedures, the operator relieves the flexure by a pull-back operation and a twist of the insertion section that has been flexed by the buckling, to change the buckling part to be substantially straight. Alternatively, as another example of such procedures, the operator or assistant applies a manual pressure by pressing the buckling part of the insertion section over the abdomen, to maintain the buckling part in a substantially straight shape.

However, for cases where buckling cannot be avoided merely by the operator's procedures, examples of methods include a first method that uniformly increases the bending stiffness of the insertion section, and a second method that uses an overtube. Thereby, the insertion section maintains a substantially straight state and the hand side force is easily transmitted to the distal end side of the insertion section, allowing the insertion section to be inserted toward a deep portion.

However, since the first method uniformly increases the bending stiffness of the insertion section, the bending stiffness of the insertion section cannot be changed according to the bending state of the entire length of the large intestine. Accordingly, the large intestine may be extended excessively in a large intestine part at which the insertion section should be advanced with a low bending stiffness, causing distress to the patient. That is, the first method is inconvenient for insertion into a deep portion.

In the second method, the outer diameter of the insertion section increases, causing an increase in the patient's distress. Also, the operator needs to operate the overtube according to a push operation of the insertion section or a pull operation of the insertion section. This decreases the operability.

On the other hand, Jpn. Pat. Appln. KOKOKU Publication No. 61-37931, for example, discloses a flexible, elongated insertion section that is divided into a plurality of segments arranged in a column shape along the axial direction and having different bending stiffnesses. According thereto, the patient's distress is reduced, and the insertability of the insertion section into a deep portion is improved.

Japanese Patent No. 4009519, for example, discloses an endoscope that changes the bending stiffness of an insertion section by suitably changing the diameter of the insertion section. According thereto, the sigmoid colon or the transverse colon can be advantageously shortened or straightened.

BRIEF SUMMARY OF THE INVENTION

A flexible tube insertion apparatus according to an embodiment of the present invention includes an insertion section that is divided into a plurality of segments arranged in a column shape along a longitudinal axis direction of the insertion section and that is inserted into a subject; one or more stiffness variable portions provided in at least one of the segments and configured to change a bending stiffness of the insertion section in units of the segments; a detection unit that detects state information of the insertion section including at least shape information of the insertion section; a bending information calculator that calculates, based on the shape information of the insertion section, bending information of the insertion section including information on a magnitude of a bend of the insertion section; a main determiner that determines, based on the magnitude of the bend of the insertion section and a threshold value set in advance for the magnitude of the bend, whether or not a bent part is present in the insertion section, and a position of the bent part in the insertion section when the bent part is present; and a controller that performs control to increase a stiffness of the stiffness variable portion provided in the segment located in the bent part, when the main determiner determines that the bent part is present and the segment provided in the stiffness variable portion is located in the bent part.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute apart of the specification, illustrate embodiments of the invention, and together with the general description given above and the detailed description of the embodiments given below, serve to explain the principles of the invention.

FIG. 2 is a diagram illustrating a relationship between a detection unit, a bend determiner, a controller, stiffness variable portions, a display apparatus, and an input apparatus.

FIG. 3I is a diagram showing control of the stiffness of the stiffness variable portions corresponding to segments located ahead of and behind the segments arranged in the bent parts.

FIG. 4B is a diagram showing a state in which the insertion section is inserted into a tube for insertion toward a deep portion at a time T2 later than the time T1.

FIG. 6A is a diagram illustrating a relationship between a detection unit, a bend determiner, a controller, a stiffness variable portion, a display apparatus, and an input apparatus, according to a third modification of the first embodiment.

DETAILED DESCRIPTION OF THE INVENTION

Figure 1:
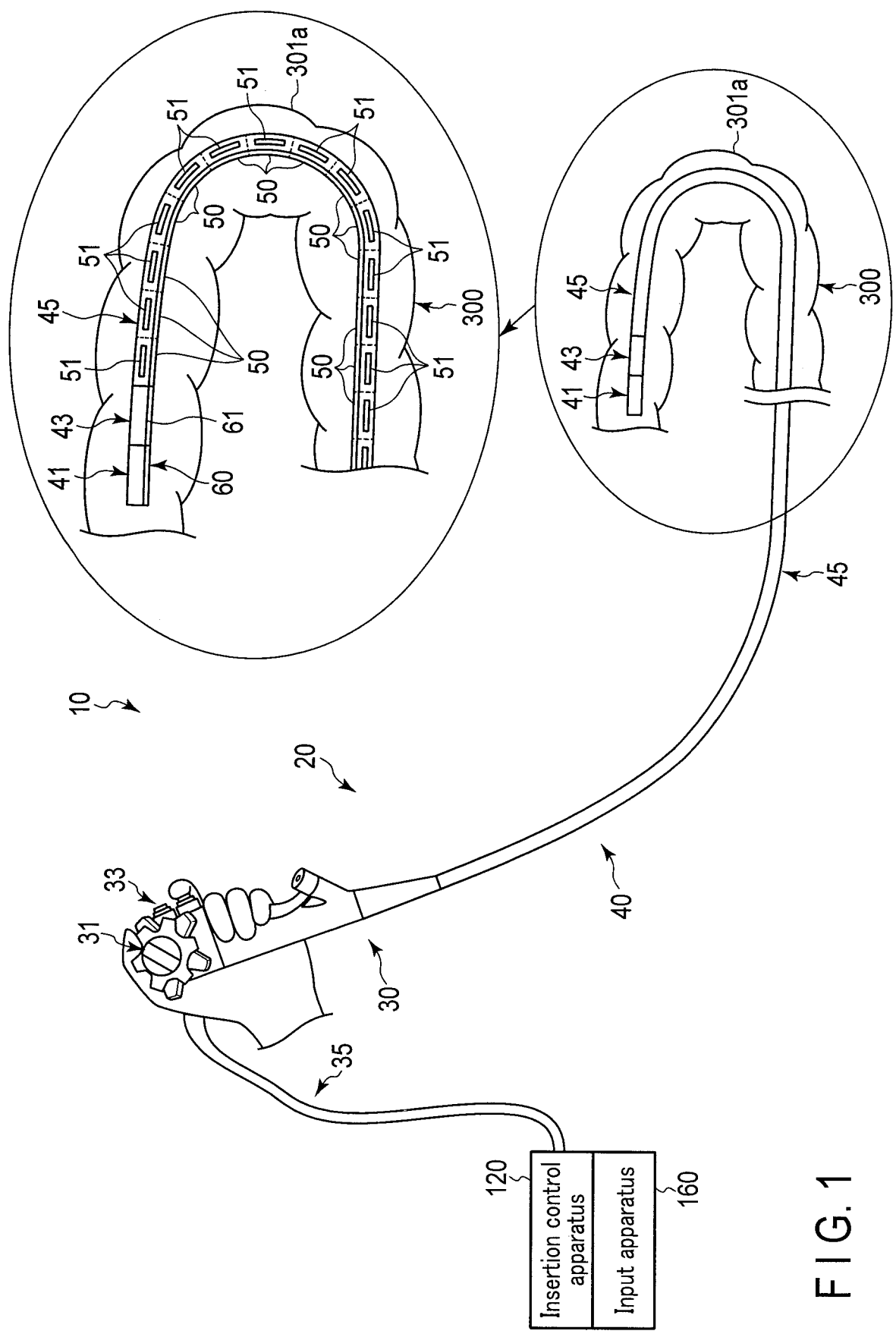
FIG. 1 is a schematic diagram of a flexible tube insertion apparatus according to a first embodiment of the present invention.

Hereinafter, embodiments of the present invention will be explained in detail with reference to the accompanying drawings. In FIG. 1, illustration of a state calculator 63 is omitted. Likewise, in some of the drawings, illustration of some members is omitted for clarification of the illustration. The deep portion refers to a position ahead of the current position as viewed in the insertion direction of an insertion section 40.

First Embodiment

Configuration

An explanation will now be given of the first embodiment, with reference to the accompanying drawings.

An flexible Tube Insertion Apparatus (hereinafter referred to as an insertion apparatus 10), which is an endoscope apparatus as shown in FIG. 1, is installed in, for example, an operation room or an examination room. The insertion apparatus 10 comprises an endoscope 20 for medical use and an insertion control apparatus 120 connected to the endoscope 20. The insertion apparatus 10 includes a display apparatus 140 (see FIG. 3B) connected to the insertion control apparatus 120 and an input apparatus 160 connected to the insertion control apparatus 120. The insertion apparatus 10 includes a light source apparatus (not shown in the drawings) connected to the endoscope 20.

The endoscope 20 is, for example, an example of an insertion apparatus that is inserted into a subject including a tube (tube portion) 300, which is the large intestine, for example. The endoscope 20 images the inside of the tube 300 using an imager (imaging portin) of an imaging unit (not shown in the drawings). The imager includes, for example, a CCD.

The light source apparatus (not shown in the drawings) emits light to allow the imager to perform imaging. The light is guided to an illumination portion (not shown in the drawings) of the illumination unit by a light guide (light guide member) (not shown in the drawings) of the illumination unit provided inside the endoscope 20. The light is emitted from the illumination portion toward an outside of the endoscope 20 as illumination light. An image taken by the imager is output to an image control apparatus (not shown in the drawings) from the imager via a signal line of the imaging unit provided inside the endoscope 20.

The image control apparatus (not shown in the drawings) performs signal processing in such a manner that the image taken by the imager is displayed on a display apparatus (not shown in the drawings).

The insertion control apparatus 120 controls the bending stiffness of the insertion section 40 provided in the endoscope 20; however, the details will be described later.

The display apparatus 140 displays the image taken by the imager and image-processed by the image control apparatus. The display apparatus 140 includes, for example, a monitor.

The input apparatus 160 is used to input various start instructions that will be described later.

The endoscope 20 will be explained as a medical flexible endoscope as an example, but is not limited thereto. The endoscope 20 may be an industrial flexible endoscope. A catheter, a treatment instrument or the like may be used instead of the endoscope 20. The endoscope 20, the catheter, the treatment instrument or the like are only required to include a flexible insertion section 40 to be inserted into a subject. The subject is not limited to, for example, a human, and may be an animal or any other structural object. The endoscope 20 may be a front-viewing endoscope 20, or a side-viewing endoscope 20.

The endoscope 20 includes an operation section 30 gripped by the operator and an insertion section 40 to be inserted into the subject.

The operation section 30 is continuous with a proximal end portion of the insertion section 40. The operation section 30 includes a bending operation portion 31 used to operate a bendable portion 43 that will be described later, and a switch portion 33 used to operate a plurality of units such as the imaging unit. The operation section 30 further includes a universal cord 35, and is connected, via the universal cord 35, to the light source apparatus (not shown in the drawings), the image control apparatus (not shown in the drawings), and the insertion control apparatus 120.

The insertion section 40 is tubular, elongated, and flexible. The insertion section 40 advances toward and retreats from the tube 300 inside the tube 300. The insertion section 40 is bendable along the tube 300. The insertion section 40 includes a distal rigid portion 41, the bendable portion 43, and a flexible tube 45 in this order from a distal end portion of the insertion section 40 toward a proximal end portion of the insertion section 40. A proximal end portion of the distal rigid portion 41 is coupled to a distal end portion of the bendable portion 43, a proximal end portion of the bendable portion 43 is coupled to a distal end portion of the flexible tube 45, and a proximal end portion of the flexible tube 45 is coupled to the operation section 30. The imager and the illumination portion are provided inside the distal rigid portion 41.

When the endoscope 20 is for medical use, the tube 300 is the large intestine, a tract, or the like. When the endoscope 20 is for industrial use, the tube 300 is a conduit, a pipe, or the like.

The bendable portion 43 actively bends in a desired direction in response to an operation on the bending operation portion 31. When an external force is applied to the bendable portion 43, the bendable portion 43 can be passively bent by the external force. The bendable portion 43 that is flexed by such an external force can be bent to follow the shape inside of the tube 300. The flexible tube 45 has flexibility, and can be passively bent by an external force. Accordingly, the flexible tube 45 that is flexed by an external force can be bent to follow the shape inside of the tube 300. The flexible tube 45 has a length greater than that of the distal rigid portion 41 or the bendable portion 43. The distal end portion of the flexible tube 45 may include the distal rigid portion 41 or the bendable portion 43, and functions as a distal end portion of the insertion section 40. The insertion section 40 is inserted into the subject from the distal end portion of the insertion section 40.

The flexible tube 45 of the insertion section 40 is divided into a plurality of segments 50 arranged in a column shape along a longitudinal axis direction of the insertion section 40. The segments 50 may function as non-existent virtual regions, or may function as existent structures.

The bending stiffness of each segment 50 can be independently changed under control of the stiffness controller (hereinafter referred to as a controller (control portion) 127 (see FIG. 2)), which will be described later, arranged in the insertion control apparatus 120. The bending stiffness of the flexible tube 45 may be partially changed by the bending stiffness of the segments 50 independently controlled by the insertion control apparatus 120.

The segments 50 are obtained by dividing the flexible tube 45, but are not limited thereto, and the segments 50 may be obtained by dividing the insertion section 40. It is thereby possible to partially change the bending stiffness of the insertion section 40 based on the bending stiffness of each of the segments 50 independently controlled by the controller 127.

The insertion apparatus 10 includes one or more stiffness variable portions 51 that can be changed in stiffness. The stiffness variable portions 51 are incorporated into the respective segments 50. The stiffness variable portions 51 may be incorporated into all the segments 50, or may be incorporated into only some of the segments 50. The area at which the stiffness variable portion 51 is provided may function at least as the segment 50. One stiffness variable portion 51 may be integrally incorporated into a plurality of segments 50. The stiffness variable portions 51 may be arranged in a line along the longitudinal axis direction of the insertion section 40, or may be arranged in a plurality of lines. When the stiffness variable portions 51 are arranged in a plurality of lines, the stiffness variable portions 51 may be provided at the same position in such a manner that the stiffness variable portions 51 are adjacent to each other as viewed in the circumferential direction of the flexible tube 45, or may be provided so as to be shifted as viewed in the longitudinal axis direction of the insertion section 40. The stiffness variable portions 51 are only required to change the bending stiffness of the insertion section 40 in units of segments, according to a change in stiffness of the stiffness variable portions 51.

Although not shown, the stiffness variable portion 51 is configured by, for example, an actuator including a coil pipe formed by a metal line and a conductive electroactive polymer artificial muscle (hereinafter referred to as EPAM) sealed inside the coil pipe. The central axis of the coil pipe is provided to match a central axis of the insertion section 40, or in parallel therewith. The coil pipe includes electrodes provided on both end portions of the coil pipe.

The electrodes are connected to the insertion control apparatus 120 via a signal cable (not shown in the drawings) incorporated into the endoscope 20, and receive electric power supplied from the insertion control apparatus 120. When a voltage is applied to the EPAM via the electrodes, the EPAM extends and contracts along the central axis of the coil pipe. However, the EPAM is restricted from extending and contracting by the coil pipe. Thereby, the stiffness of the stiffness variable portion 51 changes. The stiffness of the stiffness variable portion 51 increases as the value of the applied voltage increases. When the stiffness of the stiffness variable portion 51 changes, the bending stiffness of the segments 50 incorporating the stiffness variable portions 51 also changes in accordance therewith. Electric power is independently supplied to the respective electrodes. Accordingly, the stiffness variable portions 51 independently change in stiffness, and the segments 50 also independently change in bending stiffness. In this manner, the stiffness variable portions 51 change the bending stiffness of the segments 50 according to the change in stiffness of the stiffness variable portions 51, and partially change the bending stiffness of the flexible tube 45 according to the change in bending stiffness of the segments 50.

As the stiffness variable portion 51, a shape memory alloy may be used, instead of the EPAM.

As shown in FIGS. 1 and 2, the insertion apparatus 10 includes a detection unit (detector) 60 that detects state information of the insertion section 40 including at least the shape information of the insertion section 40. The detection unit 60 starts detection upon receiving start instructions (a detection start instruction and a calculation start instruction that will be described later) from the input apparatus 160, and constantly performs the detection. The detection timing may be every predetermined passage of time, and is not particularly limited.

The detection unit 60 includes a state detector (state detection portion) 61 arranged inside the insertion section 40, as shown in FIG. 1, and a state calculator (state calculation portion) 63 arranged in the insertion control apparatus 120, as shown in FIG. 2.

The state detector 61 detects state information of the insertion section 40 including shape information and twist information of the insertion section 40. The shape information of the insertion section 40 refers to, for example, the shape of the insertion section 40 as viewed in the longitudinal axis direction of the insertion section 40. The state detector 61 includes, for example, at least one of a coil, an output portion, an optical fiber sensor, a strain sensor, and an absorption member. The coil generates a magnetic field in response to the state of the insertion section 40, such as the shape of the insertion section 40. The output section outputs electromagnetic waves or ultrasound waves in response to the state of the insertion section 40. The optical fiber sensor can be changed in progress ratio of light in response to the state of the insertion section 40. The absorption member absorbs X-rays in response to the state of the insertion section 40.

The state detector 61 constantly performs a detection (operation) after the detection start instruction output from the input apparatus 160 is input to the state detector 61. The state detector 61 is connected to the state calculator 63 by wire or by wireless, for example, and outputs the detection result detected by the state detector 61 to the state calculator 63.

The state calculator 63 calculates state information of the insertion section 40 on the basis of the detection result of the state detector 61. As shown in FIG. 3C, assuming that, for example, bent portions in the tube 300 which is the subject are bent portions 301a and 301b, the bent portion 301a is located ahead of the bent portion 301b as viewed in the insertion direction of the insertion section 40. In the present embodiment, an explanation is made using two bent portions 301a and 301b; however, the number of the bent portions is not particularly limited thereto.

The state calculator 63 constantly performs a calculation (operation) after the calculation start instruction output from the input apparatus 160 is input to the state calculator 63. The state calculator 63 is connected to the display apparatus 140, and outputs a calculation result calculated by the state calculator 63 to the display apparatus 140. As shown in FIGS. 3B and 3D, the display apparatus 140 displays the current state information of the insertion section 40 the inside of the tube 300, on the basis of the calculation result calculated by the state calculator 63. The display is performed in a three-dimensional manner, for example. The operator is capable of monitoring the shape of the insertion section 40 the inside of the tube 300 on the basis of the state information of the insertion section 40 displayed on the display apparatus 140.

The state calculator 63 is connected to a bend determiner 121 and the controller 127, which will be described later, and outputs a calculation result calculated by the state calculator 63 to the bend determiner 121 and the controller 127.

As shown in FIG. 2, the insertion apparatus 10 includes the bend determiner (bend determination portion) 121 arranged in the insertion control apparatus 120. The bend determiner 121 determines whether or not the bent parts 201a and 201b (see FIG. 3E) are present in the insertion section 40, on the basis of the shape information of the insertion section 40 calculated by the state calculator 63. In this case, the parts including the shaded stiffness variable portions 51 in FIG. 3E are the parts determined by the bend determiner 121 as the bent parts 201a and 201b. In the explanation that follows, let us assume that the bent part 201a is located ahead of the bent part 201b as viewed in the insertion direction of the insertion section 40. In the present embodiment, an explanation is given using two bent parts 201a and 201b; however, the number of the bent parts is not particularly limited thereto. The bend determiner 121 starts a determination when a determination start instruction is input from the input apparatus 160, and constantly performs the determination. The determination timing may be every predetermined passage of time, and is not particularly limited.

As shown in FIG. 2, the bend determiner 121 includes a bending information calculator (bending information calculation portion) 123 that calculates bending information of the insertion section 40 on the basis of the shape information of the insertion section 40, and a main determiner (determination main portion) 125 that determines whether or not the bent parts 201a and 201b are present on the basis of the bending information.

The bending information represents at least one of a magnitude of the bend of the insertion section 40 and a direction of the bend of the insertion section 40. In the present embodiment, the magnitude of the bend of the insertion section 40 represents, for example, a radius of curvature or a curvature. In the present embodiment, the bending information represents a radius of curvature of the magnitude of the bend of the insertion section 40. The bending information includes, for example, a bend curve expressed by the solid or dotted lines shown in FIG. 3F, for example. The bend curve expresses a relationship between each position of the insertion section 40 and the radius of curvature of the insertion section 40. The radius of curvature is calculated on the basis of the positional information of the insertion section 40 obtained by the state detector 61. In this case, the positional information refers to positional information indicating detection data that is detected at, for example, at least three given positions.

The bending information calculator 123 outputs the calculated radius of curvature to the main determiner 125 and the controller 127. The bending information calculator 123 may be included in the state calculator 63.

The main determiner 125 determines the bent parts 201a and 201b on the basis of the magnitude of the bend and a threshold value set in advance for the magnitude of the bend. As shown in FIG. 3F, for example, the main determiner 125 compares the threshold value set in advance and the radius of curvature, and determines that the parts at which the radius of curvature has fallen below the threshold value are the bent parts 201a and 201b. The main determiner 125 outputs a determination result of the main determiner 125 to the controller 127. If the main determiner 125 determines that the bent parts 201a and 201b are present, the main determiner 125 outputs, to the controller 127, the positional information of the bent parts 201a and 201b in the insertion section 40, along with the determination result. On the basis of the threshold value and the radius of curvature, the main determiner 125 determines whether or not the bent parts 201a and 201b are parts that may be bent by buckling, for example, and whether or not a bend has been caused in the course of insertion.

The bent parts 201a and 201b are parts of the insertion section 40 in the bend curve located below the threshold value, and are stiffness variable regions whose bending stiffness can be changed by the controller 127, which will be described later. The bent parts 201a and 201b are parts of the insertion section 40 other than the substantially straight parts 203a and 203b (see FIGS. 3F and 3G), which include a straight part (not shown in the drawings).

The threshold value indicates the degree of the bend of the bent parts 201a and 201b. The threshold value is stored in advance in, for example, a storage (storage portion) (not shown in the drawings) and is suitably read by the main determiner 125 from the storage. The threshold value may be input from, for example, the input apparatus 160 to the main determiner 125. The threshold value may be suitably set in accordance with the tube 300. The threshold value suitably differs according to, for example, the patient.

As shown in FIG. 2, the insertion apparatus 10 includes the controller 127 arranged in the insertion control apparatus 120. The controller 127 is connected to the stiffness variable portions 51 via a signal cable (not shown in the drawings) incorporated into the endoscope 20 including the universal cord 35.

Figure 3A:
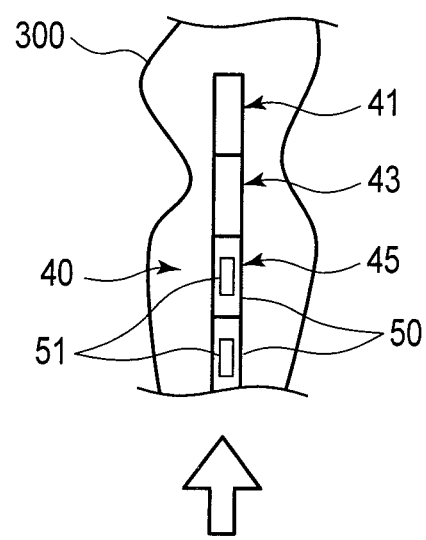
FIG. 3A is a diagram showing a state in which the insertion section is inserted into a tube for insertion toward a deep portion.
Figure 3B:
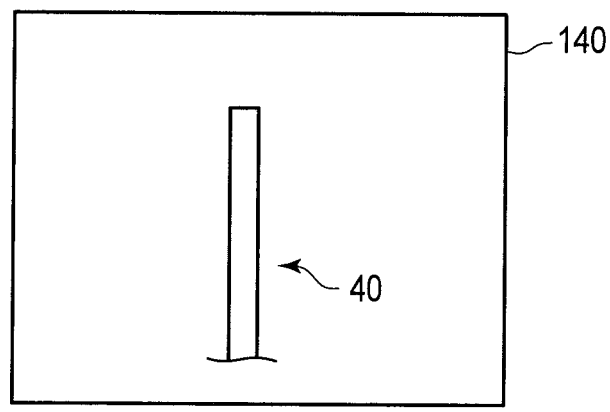
FIG. 3B is a diagram of the insertion section displayed on a display apparatus in a state of being inserted into a tube for insertion toward a deep portion.
Figure 3C:
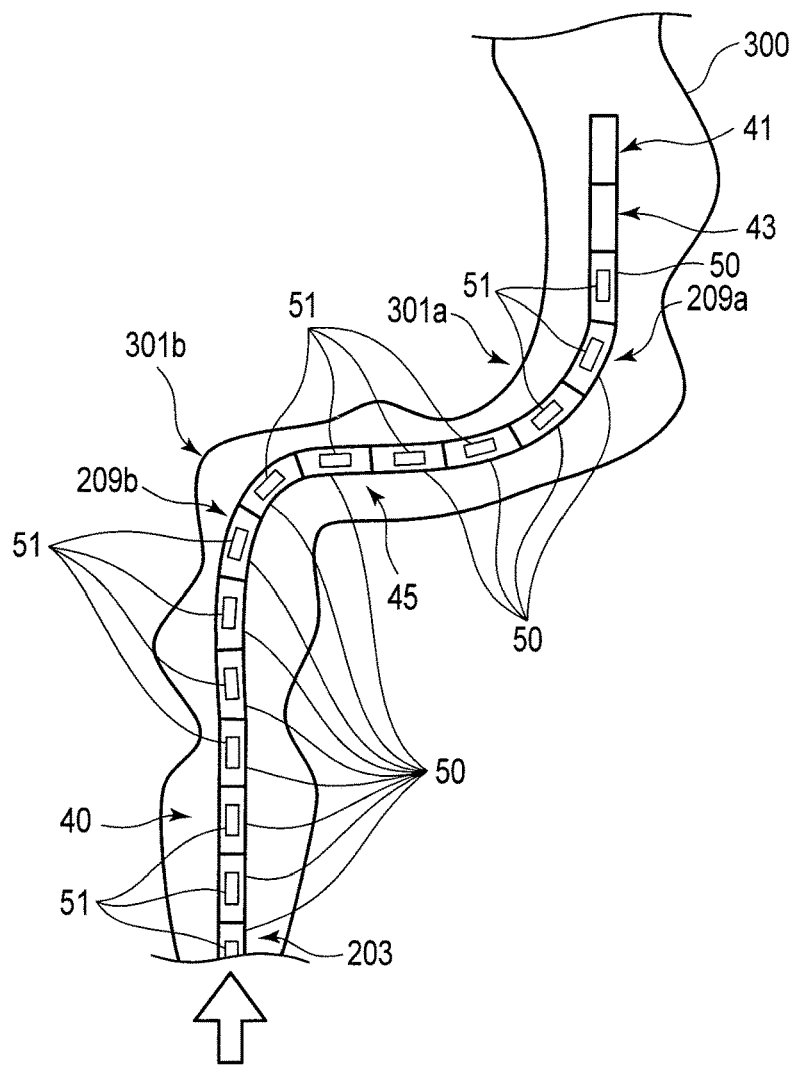
FIG. 3C is a diagram showing a state in which the insertion section is passing through bent portions of the tube.
Figure 3D:
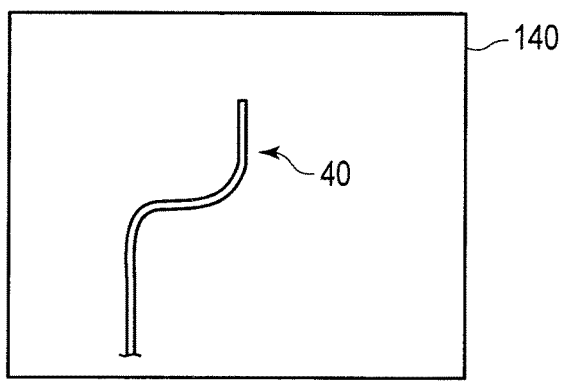
FIG. 3D is a diagram of the insertion section displayed on the display apparatus in a state of passing through the bent portions of the tube.
Figure 3E:
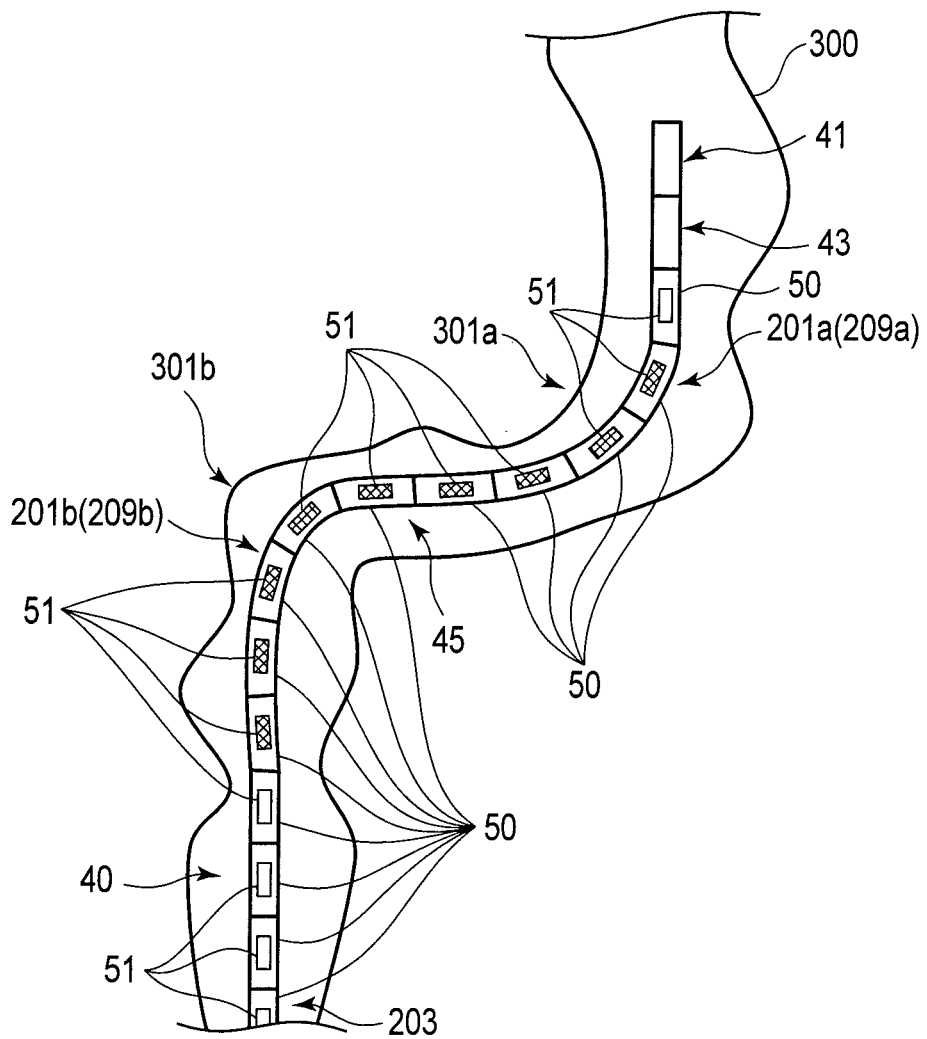
FIG. 3E is a diagram showing a state in which the bend determiner determines that bent parts are present in the insertion section.
Figure 3F:
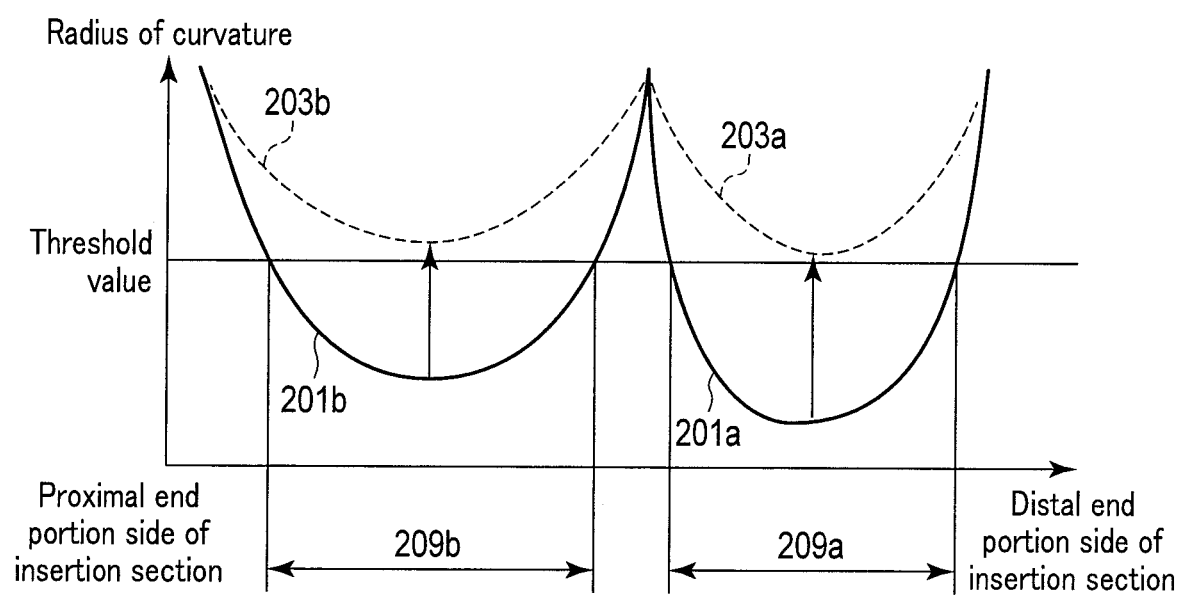
FIG. 3F is a diagram showing a state in which a stiffness of stiffness variable portions corresponding to segments arranged in the bent parts is controlled to be a substantially straight stiffness.
Figure 3G:
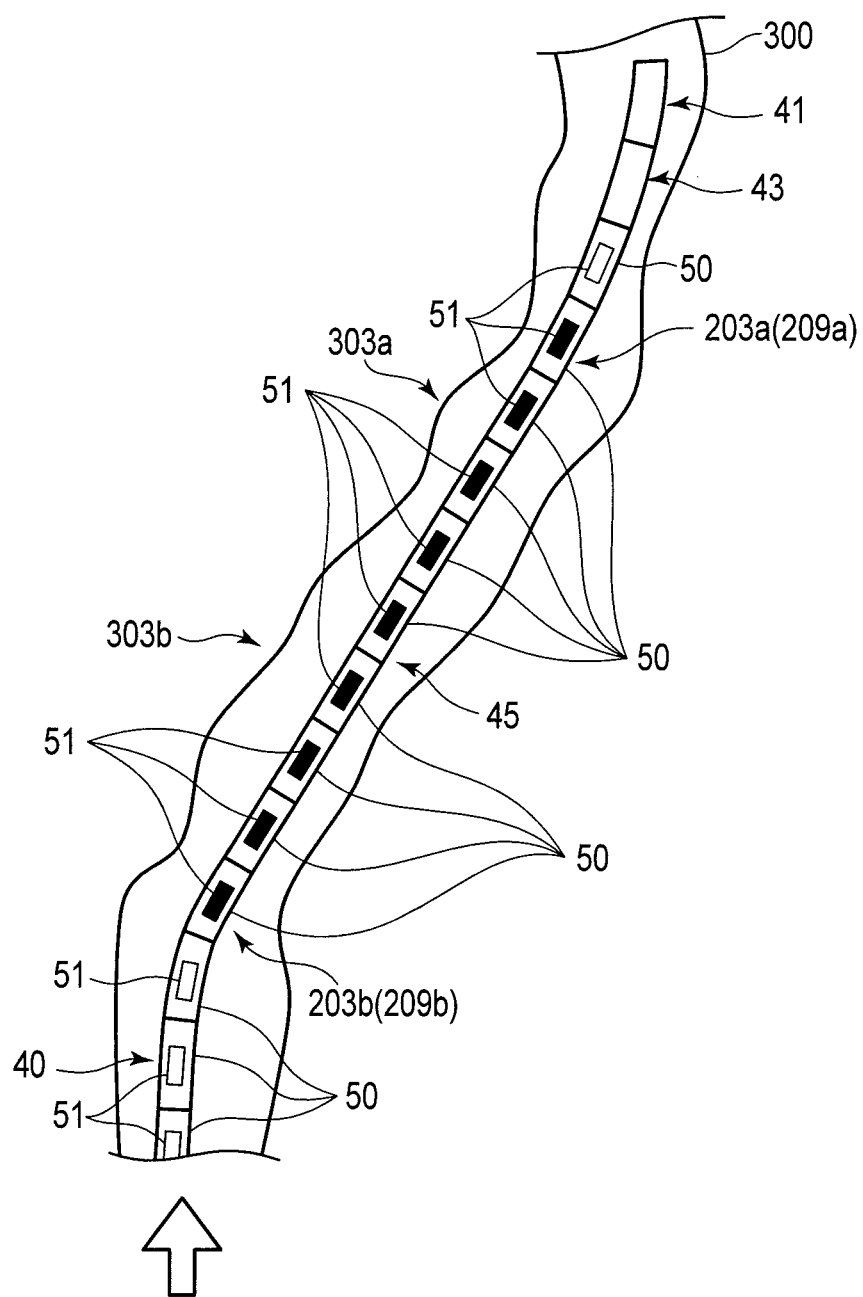
FIG. 3G is a diagram showing a state in which the bent parts have been changed to substantially straight parts based on the substantially straight stiffness.

As shown in FIGS. 3E, 3F, and 3G, when the bend determiner 121 determines that the bent parts 201a and 201b are present in the insertion section 40, the controller 127 controls the stiffness of the stiffness variable portions 51 corresponding to the segments 50 arranged in the bent parts 201a and 201b to be a stiffness that makes the bent parts 201a and 201b substantially straight. For example, the controller 127 increases the stiffness of the stiffness variable portions 51 to a stiffness that makes the bent parts 201a and 201b substantially straight, to change the bent parts 201a and 201b to substantially straight parts 203a and 203b (see FIGS. 3F and 3G). In other words, the controller 127 increases the stiffness of the stiffness variable portions 51 to a stiffness that makes the bent parts 201a and 201b substantially straight, to change the passing parts 209a and 209b, which are parts passing through the bent portions 301a and 301b, from a bent state to a substantially straight state. The passing parts 209a and 209b correspond to the bent parts 201a and 201b. In this case, the stiffness of the stiffness variable portions 51 that are indicated in black in FIG. 3G is controlled, and the substantially straight parts 203a and 203b are generated. The stiffness variable portions 51 corresponding to the segments 50 refer to, for example, the stiffness variable portions 51 provided in the segments 50, namely, the stiffness variable portions 51 of the segments 50 whose bending stiffness can be changed.

The stiffness that makes the bent parts 201a and 201b substantially straight (hereinafter referred to as a substantially straight stiffness) refers to a stiffness that changes the bent parts 201a and 201b to the substantially straight parts 203a and 203b, and that keeps the substantially straight parts 203a and 203b in the substantially straight state without causing them to be bent, even when an external force is applied to the substantially straight parts 203a and 203b. The external force refers to a force applied to the substantially straight parts 203a and 203b from a given angle with respect to the central axis of, for example, the substantially straight parts 203a and 203b. The substantially straight stiffness is higher than a stiffness that is not controlled by the controller 127. In other words, the bending stiffness of the substantially straight parts 203a and 203b is higher than the other parts in which the bending stiffness is not controlled. The substantially straight parts 203a and 203b function as high bending stiffness parts that are not bent and maintain the substantially straight state even if an external force is applied thereto. The other parts that are not controlled in bending stiffness function as low bending stiffness parts that can be passively bent upon receiving an external force. The substantially straight stiffness can be adjusted as desired according to the tube 300.

The controller 127 controls the stiffness of the stiffness variable portions 51 on the basis of the magnitude of the bend and the threshold value. As shown in FIG. 3F, for example, the controller 127 controls the stiffness of the stiffness variable portions 51 to be a stiffness that makes the radius of curvature of each of the bent parts 201a and 201b exceed the threshold value. This stiffness indicates a substantially straight stiffness. The controller 127 increases the stiffness of the stiffness variable portion 51 to a substantially straight stiffness until the radius of curvature of each of the bent parts 201a and 201b exceeds a threshold value. The controller 127 constantly receives the radius of curvature of each of the bent parts 201a and 201b input from the bending information calculator 123, and controls the stiffness on the basis of the radius of curvature and the threshold value of each of the bent parts 201a and 201b. The controller 127 suitably reads a threshold value from the storage (not shown in the drawings).

In the present embodiment, the controller 127 controls the stiffness of the stiffness variable portions 51 provided in the segments 50 arranged in all the bent parts 201a and 201b. That is, the controller 127 uniformly changes the bent parts 201a and 201b to the substantially straight parts 203a and 203b. For example, the controller 127 simultaneously starts controlling. In the bent part 201a, for example, the controller 127 may control the stiffness of the stiffness variable portion 51 provided in the segment 50 that is arranged at the center of the bent part 201a as viewed in the longitudinal axis direction of the insertion section 40. Alternatively, the controller 127 may control the bent part 201a, for example, in such a manner that the stiffness of the stiffness variable portions 51 of the entire bent part 201a becomes equal. Alternatively, the controller 127 may set a difference in stiffness in the bent part 201a, for example, in such a manner that the stiffness of the stiffness variable portion 51 provided in the segment 50 arranged at the center of the bent part 201a as viewed in the longitudinal axis direction of the insertion section 40 becomes the highest, and that the stiffness of the stiffness variable portion 51 provided in the segment 50 arranged at an end portion of the bent part 201a as viewed in the longitudinal axis direction of the insertion section 40 becomes the lowest.

The controller 127 is not limited to one that controls only the stiffness of the stiffness variable portions 51 provided in the segments 50 arranged in the bent parts 201a and 201b. For example, as shown in FIG. 3I, the controller 127 may control the stiffness of the stiffness variable portion 51 corresponding to segments 50a located ahead of and behind the segments 50 arranged in the bent parts 201a and 201b to be a substantially straight stiffness. Alternatively, the controller 127 may control the stiffness of the stiffness variable portion 51 provided in a desired segment 50 other than the segments 50 arranged in the bent part to be a desired stiffness, for example.

Figure 3H:
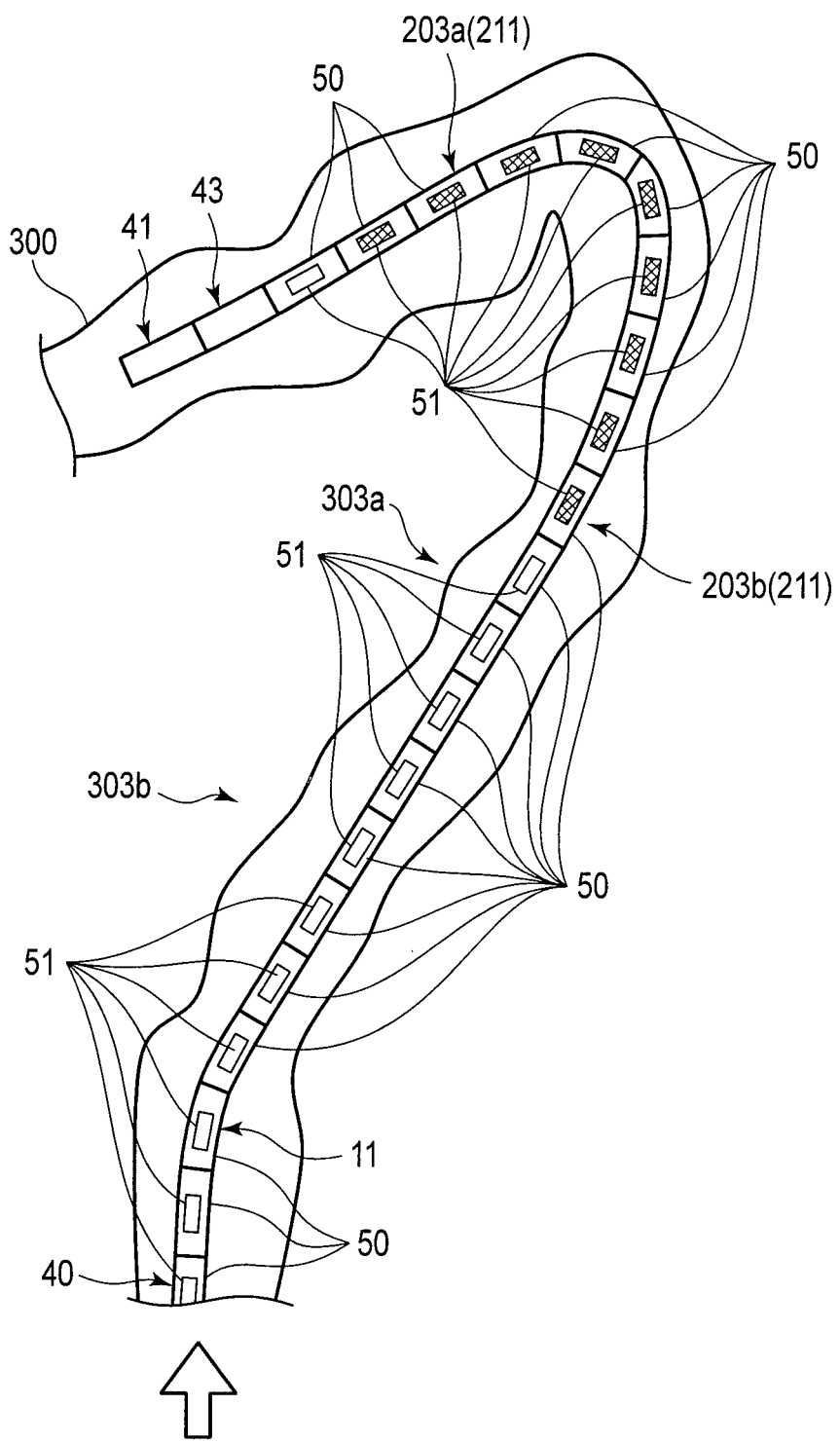
FIG. 3H is a diagram showing a state in which the stiffness of the stiffness variable portions is reset to an initial stiffness, and the insertion section is inserted toward a deep portion.
Figure 31:
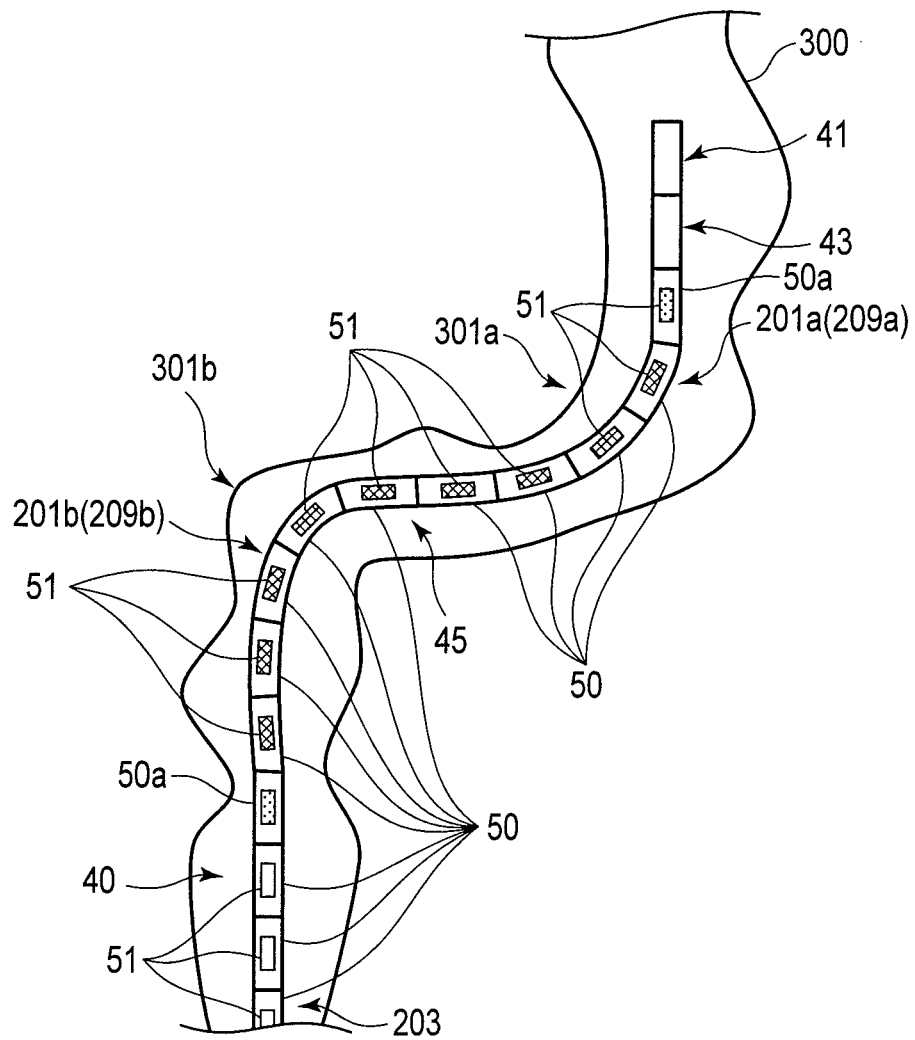

On the basis of the shape information of the insertion section 40, which is a calculation result calculated by the state calculator 63, the controller 127 controls, as desired, the stiffness of the stiffness variable portion 51 corresponding to the segment 50 that has passed through a desired part in the tube 300 and has the stiffness controlled to be substantially straight. The desired part refers to, for example, substantially straight portions 303a and 303b. For example, the controller 127 decreases the substantially straight stiffness of the stiffness variable portion 51 in the substantially straight parts 203a and 203b to a desired stiffness. In this case, the stiffness of the shaded stiffness variable portions 51 in the substantially straight parts 203a and 203b in FIG. 3H is decreased by the controller 127. Thereby, the passage completion parts 211, which are substantially straight parts 203a and 203b that have completed passing through the bent portions 301a and 301b (substantially straight portions 303a and 303b), can be bent upon receiving an external force, and become bendable along the tube 300. The desired stiffness refers to, for example, the initial stiffness before the stiffness is changed. The initial stiffness refers to a stiffness that allows the insertion section 40 to be passively bent by, for example, an external force. The initial stiffness may be a stiffness that allows the insertion section 40 to be bent along the tube 300. The desired stiffness may be zero or any value lower than the substantially straight stiffness, and may be set to a desired value again. At this time, the controller 127 may end control of the stiffness.

The controller 127 starts control upon receiving a control start instruction input from the input apparatus 160, and constantly performs the control. The control timing may be every predetermined passage of time, and is not particularly limited.

The state calculator 63, the bend determiner 121, and the controller 127 are configured by, for example, a hardware circuit including an ASIC and the like. At least one of the state calculator 63, the bend determiner 121, and the controller 127 may be configured by, for example, a processor including a CPU and the like. When at least one of them is configured by a processor, an internal memory or external memory (not shown in the drawings) that can be accessed by the processor is provided. The internal memory or external memory stores a program code that causes the processor to function as at least one of them when the processor is executed. The state calculator 63, the bend determiner 121, and the controller 127 may be configured using one processor, or may be configured using a plurality of processors. In the latter case, the processors may perform processing in association with each other, so as to transmit and receive data to and from each other. Furthermore, the processors may be arranged in different housings in the latter case.

As shown in FIG. 2, the input apparatus 160 outputs to the detection unit 60 a detection start instruction and a calculation start instruction to start detection and calculation of the detection unit 60, outputs to the bend determiner 121 a determination start instruction to start the determination of the bend determiner 121, and outputs to the controller 127 a control start instruction to start control of the controller 127. The input apparatus 160 may output a detection start instruction, a calculation start instruction, a determination start instruction, and a control start instruction either simultaneously or individually. The input apparatus 160 performs this output before the insertion is performed, namely, before control of the controller 127 is performed. The input apparatus 160 is, for example, a general input device, and is, for example, a pointing device such as a keyboard and a mouse, a tag reader, a button switch, a slider, and a dial.

When the input apparatus 160 outputs a control start instruction to the controller 127, switching of the control mode may be performed. The control mode refers to, for example, control of only the stiffness of the stiffness variable portions 51 provided in the segments 50 arranged in the bent parts 201a and 201b, or control of the stiffness of the stiffness variable portions 51 provided in the segments 50 arranged in the bent parts 201a and 201b and the segments 50 located ahead of and behind these segments 50.

After the insertion apparatus 10 is driven, the insertion section 40 is inserted into the tube 300 for insertion toward the deep portion, as shown in FIG. 3A. When the operator operates the input apparatus 160 and the input apparatus 160 outputs a detection start instruction and a calculation start instruction to the detection unit 60, the state detector 61 detects the state information of the insertion section 40 in real time. The detection result detected by the state detector 61 is output to the state calculator 63 in real time. The state calculator 63 calculates state information of the insertion section 40 in real time, on the basis of the detection result of the state detector 61. The state calculator 63 outputs a calculation result calculated by the state calculator 63 to the display apparatus 140, the bend determiner 121, and the controller 127. As shown in FIG. 3B, the display apparatus 140 displays the current state of the insertion section 40 inside of the tube 300 in real time, on the basis of the calculation result calculated by the state calculator 63. The operator monitors the shape of the insertion section 40 inside of the tube 300 on the basis of the state of the insertion section 40 displayed on the display apparatus 140.

In accordance with an operation of the bending operation portion 31 on the bendable portion 43 and the operator's push and pull operation and twist operation on the insertion section 40, the insertion section 40 passes through the bent portions 301a and 301b, as shown in FIG. 3C. As shown in FIG. 3D, the display apparatus 140 displays, using the state detector 61 and the state calculator 63, the shape of the insertion section 40 that is bent in accordance with the tube 300 and the bent portions 301a and 301b, and the insertion section 40 that passes through the bent portions 301a and 301b while bending. This situation is monitored by the operator.

For insertion of the insertion section 40 toward a deep portion under a situation where the insertion section 40 is passing through the bent portions 301a and 301b, the operator grips the proximal end portion of the insertion section 40 exposed to the outside from the tube 300, and pushes the insertion section 40 forward from the gripped part. At this time, the passing parts 209a and 209b passing through the bent portions 301a and 301b may prevent the hand side force that pushes the insertion section 40 forward from being easily transmitted to the distal end portion of the insertion section 40 from the gripped part. Thereby, buckling may occur in the passing parts 209a and 209b, reducing the insertability of the insertion section 40 into a deep portion. Accordingly, the operator operates the input apparatus 160 under the monitored situation. The input apparatus 160 outputs a determination start instruction to the bend determiner 121, and outputs a control start instruction to the controller 127.

As shown in FIGS. 3E and 3F, the bend determiner 121 determines whether or not the bent parts 201a and 201b are present in the insertion section 40 in real time, on the basis of the shape information of the insertion section 40. Specifically, the bending information calculator 123 calculates a radius of curvature, which is bending information of the insertion section 40, on the basis of the shape information of the insertion section 40 in real time, and outputs the calculated radius of curvature to the main determiner 125 and the controller 127. As shown in FIGS. 3E and 3F, the main determiner 125 compares a threshold value set in advance and a radius of curvature, determines whether or not the radius of curvature has fallen below the threshold value, and determines that the parts at which the radius of curvature has fallen below the threshold value are bent parts 201a and 201b. Let us assume that the main determiner 125 determines that the bent parts 201a and 201b are present in the insertion section 40. The main determiner 125 outputs a determination result including positional information of the bent parts 201a and 201b in the insertion section 40 to the controller 127.

The controller 127 calculates a part at which the bending stiffness should be changed in the insertion section 40, on the basis of the positional information of the bent parts 201a and 201b in the determination result. As shown in FIGS. 3F and 3G, the controller 127 controls, in real time, the stiffness of the stiffness variable portions 51 provided in the segments 50 arranged in the bent parts 201a and 201b to be a substantially straight stiffness. For example, the controller 127 controls the stiffness of the stiffness variable portions 51 to be a stiffness that makes the radius of curvature exceed the threshold value.

Thereby, the stiffness of the stiffness variable portions 51, for example, increases to a substantially straight stiffness, and the bent parts 201a and 201b change to substantially straight parts 203a and 203b, as shown in FIGS. 3F and 3G. In accordance with this change, the bent portions 301a and 301b change to substantially straight portions 303a and 303b. That is, the controller 127 changes the bent parts 201a and 201b to substantially straight parts 203a and 203b by controlling the stiffness of the stiffness variable portions 51, and changes the bent portions 301a and 301b to substantially straight portions 303a and 303b based on the substantially straight parts 203a and 203b. The controller 127 relieves the bent portions 301a and 301b. In other words, the controller 127 changes the state of the bent portions 301a and 301b as well, in accordance with the change in state of the passing parts 209a and 209b.

Under such a situation, the hand side force is efficiently transmitted from the gripped part to the distal end portion of the insertion section 40, by the substantially straight parts 203a and 203b and the substantially straight portions 303a and 303b. Accordingly, the substantially straight parts 203a and 203b are configured in such a manner that the substantially straight portions 303a and 303b are easily inserted toward a deep portion. That is, the insertion section 40 is easily advanced forward, thus improving the insertability of the insertion section 40. Since the substantially straight parts 203a and 203b have a high bending stiffness, the hand side force is efficiently transmitted to the distal end portion of the insertion section from the gripped part. This prevents occurrence of buckling, and improves the insertability of the insertion section 40 into a deep portion.

The stiffness of the stiffness variable portion may not increase and the bent parts 201a and 201b attempt to pass through the bent portions 301a and 301b in a bent state. In this case, the bent parts 201a and 201b may prevent the hand side force from being easily transmitted to the distal end portion of the insertion section, buckling may occur in the bent parts 201a and 201b. Even when the passing parts 209a and 209b are substantially straight parts, buckling may occur when the bending stiffness of the substantially straight parts is low. When the bending stiffness of the substantially straight parts is low, the bent portions 301a and 301b cannot be changed to substantially straight portions, the bent portions 301a and 301b remain in a bent state, and the substantially straight parts having a low bending stiffness may not endure the pressure of the bent portions 301a and 301b and may be bent.

However, in the present embodiment, the bent parts 201a and 201b reliably change to the substantially straight parts 203a and 203b, the bent portions 301a and 301b reliably change to the substantially straight portions 303a and 303b based on the substantially straight parts 203a and 203b, and the bending stiffness of the substantially straight parts 203a and 203b is increased by the change in stiffness of the stiffness variable portions 51. This prevents a bend of the substantially straight parts 203a and 203b, the hand side force is efficiently transmitted from the gripped part to the distal end portion of the insertion section 40, and the insertion section 40 is easily inserted toward a deep portion, thus improving the insertability of the insertion section 40. Furthermore, since the hand side force is efficiently transmitted from the gripped part to the distal end portion of the insertion section 40, occurrence of buckling is prevented, and the insertability of the insertion section 40 into a deep portion is improved.

Although not shown, the tube 300 is the large intestine, for example, and when the insertion section 40 is passing through the sigmoid colon, which is represented by the bent portions 301a and 301b, the passing parts 209a and 209b passing through the sigmoid colon in the insertion section 40 are the bent parts 201a and 201b. By the change in stiffness of the stiffness variable portion 51, the bent parts 201a and 201b change to the substantially straight parts 203a and 203b, and the sigmoid colon (bent portions 301a and 301b) change to the substantially straight portions 303a and 303b by the substantially straight parts 203a and 203b. The bending stiffness of the substantially straight parts 203a and 203b is increased by the change in stiffness of the stiffness variable portions 51. This prevents a bend of the substantially straight parts 203a and 203b, the hand side force is efficiently transmitted from the gripped part to the distal end portion of the insertion section 40, and thereby occurrence of buckling is prevented. Thus, the insertion section 40 is easily inserted toward the transverse colon located in a deep portion of the large intestine than the sigmoid colon, and thereby the insertability of the insertion section 40 is improved. When the insertion section 40 that has passed through the sigmoid colon passes through the transverse colon, the bent parts corresponding to the sigmoid colon and the transverse colon are respectively changed to substantially straight parts, and the sigmoid colon and the transverse colon are changed to substantially straight portions by the substantially straight parts. This facilitates insertion toward the ascending colon located in a deep portion of the large intestine than the transverse colon, and improves the insertability of the insertion section 40.

The sigmoid colon and the transverse colon, for example, of the large intestine are not fixed within the abdomen, and are easily moved inside the abdomen. In particular, insertion into the flexible and easily bendable large intestine, which is moved by an insertion operation of the insertion section 40, is not easy. However, the insertion section 40 is easily inserted toward a deep portion, as described above. Thus, the insertability is improved even if the state of the tube 300 changes in accordance with insertion of the insertion section 40.

When the substantially straight parts 203a and 203b have completed passing through the substantially straight portions 303a and 303b, for example, the controller 127 determines the passage on the basis of the calculation result (shape information of the insertion section 40) of the state calculator 63. As shown by the shading in FIG. 3H, the controller 127 decreases the substantially straight stiffness of the stiffness variable portions 51 provided in the segments 50 that are arranged in the passage completion parts 211, which are substantially straight parts 203a and 203b that have completed passing through the substantially straight portions 303a and 303b and have a substantially straight stiffness, to a desired stiffness. For example, the controller 127 resets the controlled stiffness of the stiffness variable portions 51 to the initial stiffness. Thereby, the passage completion part 211 is relieved from the substantially straight state, returns to the low bending stiffness part, and becomes bendable upon receiving an external force. Accordingly, the insertion section 40 can be bent along the tube 300. Let us assume that the operator monitors the state of the insertion section 40 via the display apparatus 140. Under such a situation, the operator may operate the input apparatus 160, and stop outputting various start instructions from the input apparatus 160. Thereby, the passage completion part 211 is relieved from the substantially straight state, returns to the low bending stiffness part, and becomes bendable upon receiving an external force.

Although not shown, when a rear part located behind the passage completion parts 211 as viewed in the insertion direction passes through the bent portions 301a and 301b, the above-described operations of the bend determiner 121 and the controller 127 are repeated. Accordingly, as the insertion section 40 is inserted, the critical part (position) of the insertion section 40 that changes in bending stiffness may be shifted backward; however, the controller 127 changes (switches) the stiffness variable portion 51 that changes in stiffness, in such a manner that the portion of the insertion section 40 that changes in bending stiffness does not relatively change with respect to the bent portions 301a and 301b. At this time, the controller 127 controls the stiffness variable portions 51 in such a manner that the stiffness variable portion 51 that changes in stiffness is shifted from the stiffness variable portion 51 that is passing through the bent portions 301a and 301b and the stiffness variable portion 51 that is to pass through the bent portions 301a and 301b. Thus, when the insertion section 40 passes through the bent portions 301a and 301b, the bending stiffness of the insertion section 40 in the passing parts 209a and 209b that are passing through the bent portions 301a and 301b constantly change. The part is only required to include at least one segment 50. Thereby, the part that changes in bending stiffness does not relatively change with respect to the bent portions 301a and 301b, and the bending stiffness of the insertion section 40 in the passing parts 209a and 209b that pass through the bent portions 301a and 301b constantly change.

Even after the substantially straight parts 203a and 203b have completed passing through the substantially straight portions 303a and 303b, the controller 127 may maintain the substantially straight stiffness of the stiffness variable portions 51 in the substantially straight parts 203a and 203b.

According to the present embodiment, the bent parts 201a and 201b corresponding to the shape of the bent portions 301a and 301b are detected and determined, and the stiffness of the stiffness variable portions 51 is controlled in such a manner that the bent parts 201a and 201b change to a substantially straight state. Accordingly, in the present embodiment, the bent parts 201a and 201b can be changed to the substantially straight parts 203a and 203b, and the hand side force can be efficiently transmitted from the gripped part to the distal end portion of the insertion section 40 by the increase in bending stiffness of the substantially straight parts 203a and 203b, thus improving the insertability of the insertion section 40 into a deep portion. In the present embodiment, since the bending stiffness of the substantially straight parts 203a and 203b can be increased and the hand side force can be efficiently transmitted to the distal end portion of the insertion section 40 from the gripped part, it is possible to prevent occurrence of buckling and to improve insertability of the insertion section 40 into a deep portion. In the present embodiment, it is possible to improve the insertability of the insertion section 40 into a deep portion, even if the state of the tube 300 changes in accordance with the insertion of the insertion section 40 into a deep portion. In the present embodiment, since the occurrence of buckling can be prevented, it is possible to insert the insertion section 40 into a patient in a less-invasive manner. In the present embodiment, since the insertability of the insertion section 40 can be improved, it is possible to reduce the burden on the operator who operates the insertion apparatus 10.

In the present embodiment, the bent parts 201a and 201b are uniformly changed to a substantially straight state. It is thus possible to eliminate hard-to-acquire procedures or complicated procedures for changing the bent parts 201a and 201b into a substantially straight state. Examples of such procedures include a procedure of changing the buckling part to substantially straight parts 203a and 203b by retreating the insertion section 40 by pulling, or the operator's or assistant's manual pressure that pushes the buckling part over the abdomen.

In the present embodiment, it is possible to change the bent parts 201a and 201b to substantially straight parts 203a and 203b with ease and safety, without burdening the operator.

In the present embodiment, the main determiner 125 determines the presence of the bent parts 201a and 201b on the basis of the bending information. Accordingly, the bent parts 201a and 201b can be determined with high precision. In the present embodiment, the main determiner 125 determines that the parts at which the radius of curvature is below the threshold value are bent parts 201a and 201b. Accordingly, the load on the controller 127 that controls the stiffness of the stiffness variable portion 51 can be reduced. In the present embodiment, the controller 127 controls the stiffness of the stiffness variable portion 51 to be a stiffness that makes the radius of curvature exceed the threshold value. Accordingly, when the stiffness of the stiffness variable portion 51 is changed, the stiffness can be reliably defined.

In the present embodiment, when the substantially straight parts 203a and 203b have completed passing through the substantially straight portions 303a and 303b, the passage completion parts 211, which are substantially straight parts 203a and 203b, are relieved from the substantially straight state and return to the low bending stiffness parts. This allows the passage completion parts 211 to be bent along the tube 300, thus improving the insertability.

In the present embodiment, when the rear part located behind the passage completion parts 211 passes through the bent portions 301a and 301b, the above-described operations of the bend determiner 121 and the controller 127 are repeated. It is thus possible to constantly change the bending stiffness of the insertion section 40 in the bent parts 201a and 201b at the timing of passing through the bent portions 301a and 301b, thus constantly improving the insertability.

For example, once a control start instruction is input to the controller 127, the controller 127 continues changing the stiffness of the stiffness variable portions 51 in real time; however, the configuration is not limited thereto. The controller 127 may change the stiffness of the stiffness variable portions 51 only at a timing when the control start instruction is input.

While the radius of curvature is used in the present embodiment, the curvature may be used instead. The curvature is the reciprocal of the radius of curvature. Accordingly, the main determiner 125 compares the threshold value set in advance and the curvature, and determines that the part at which the curvature is above a threshold value is the bent parts 201a and 201b. The controller 127 controls the stiffness of the stiffness variable portions 51 to be a stiffness that makes the curvature of each of the bent parts 201a and 201b fall below the threshold value.

First Modification

A first modification of the first embodiment will be explained with reference to FIGS. 4A, 4B, and 4C. In the present modification, only the features different from those of the first embodiment will be described.

Bending information of the present modification represents a radius of curvature that is a magnitude of a bend of an insertion section 40. An input apparatus 160 outputs a comparison start instruction, which is an instruction to start comparison, to a main determiner 125, at a time T1 (see FIGS. 4A and 4C), which is a start time of a desired period of time. The input apparatus 160 outputs a length of the desired period of time to the main determiner 125. The desired period of time may be set in advance.

Figure 4A:
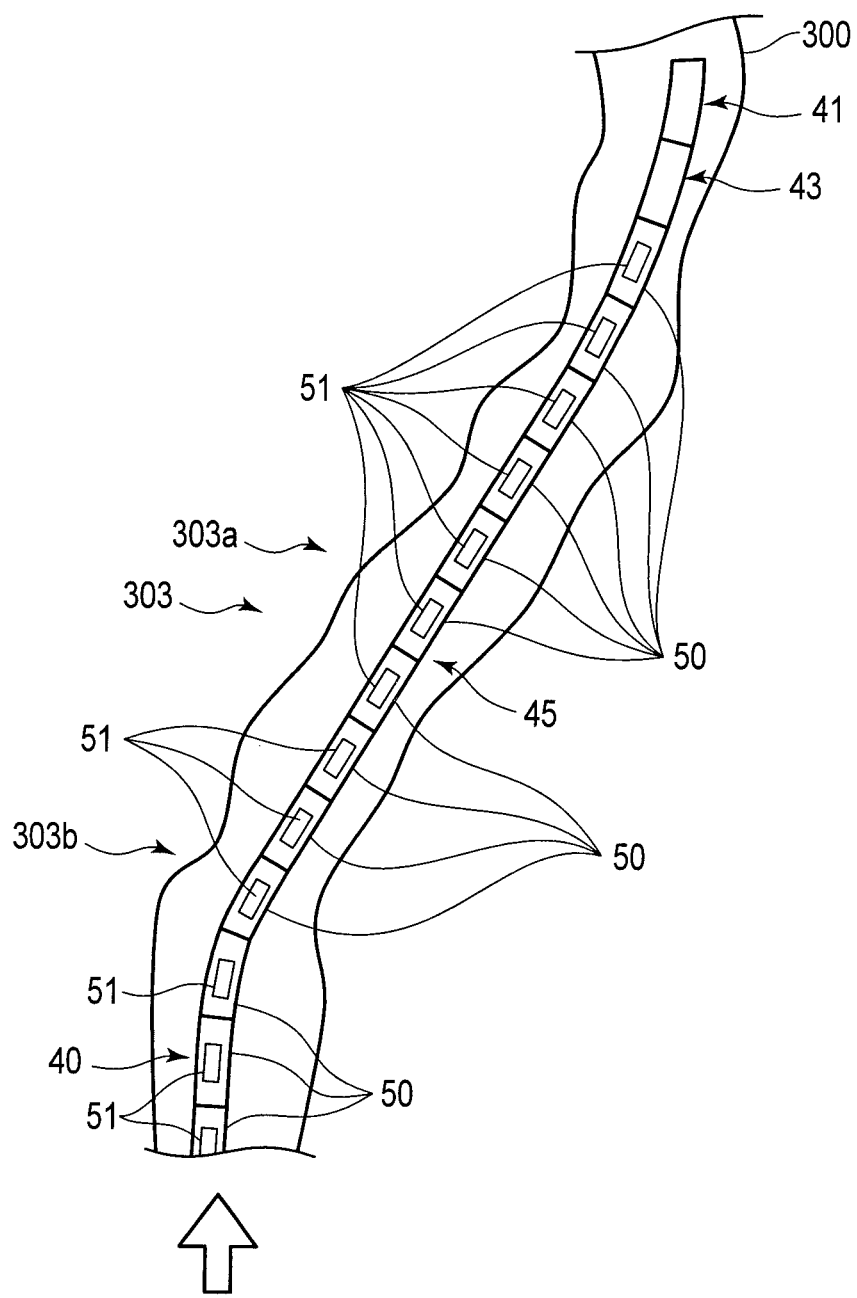
FIG. 4A is a diagram showing a state in which the insertion section is inserted into a tube for insertion toward a deep portion at a time T1, according to a first modification of the first embodiment.
Figure 4C:
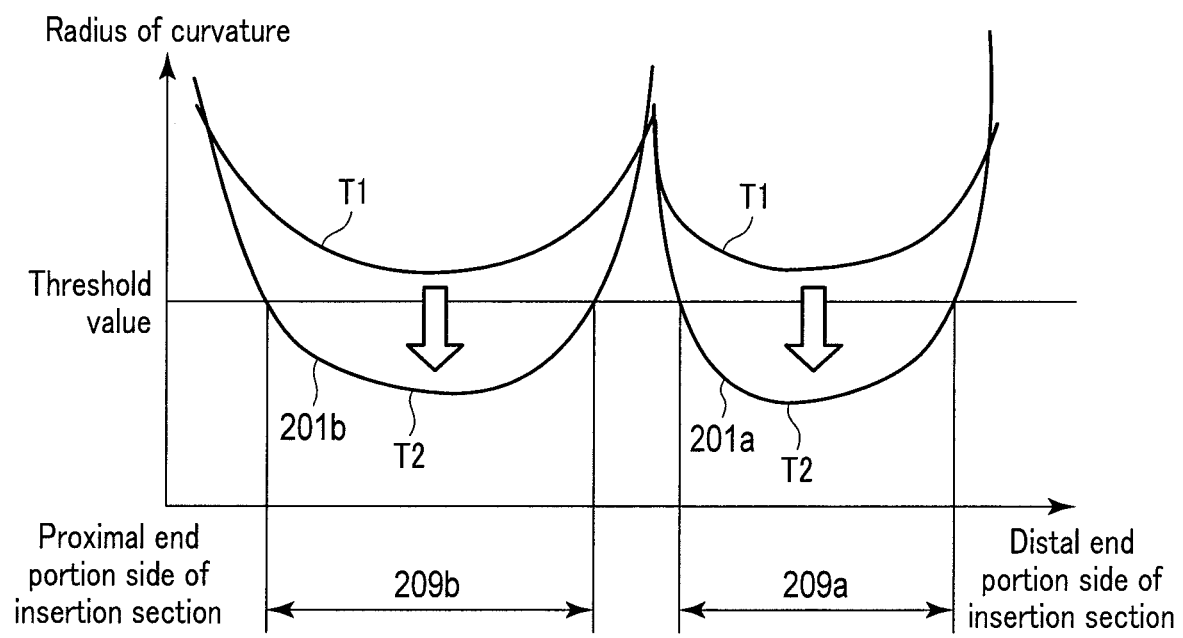
FIG. 4C is a diagram showing a state in which a change amount of a radius of curvature of the bent portions from the time T1 to the time T2 has fallen below a threshold value.

As shown in FIG. 4C, the main determiner 125 determines, on the basis of the threshold value set in advance and a change amount of the radius of curvature in the desired period of time, that the parts at which the radius of curvature has fallen below the threshold value after passage of the desired period of time are the bent parts 201a and 201b. The controller 127 controls the stiffness of the stiffness variable portions 51 until the radius of curvature exceeds a threshold value.

For example, at a time T1 shown in FIGS. 4A and 4C, the operator operates an input apparatus 160, and the input apparatus 160 outputs a comparison start instruction to the main determiner 125. Let us assume that the radius of curvature is above the threshold value at the time T1.

At a time T2 at which the desired period of time has passed from the time T1 shown in FIGS. 4B and 4C, the main determiner 125 compares the radius of curvature at the time T2 and the threshold value. When the radius of curvature at the time T2 has fallen below the threshold value, the main determiner 125 determines that the parts at which the radius of curvature is below the threshold value are bent parts 201a and 201b. The controller 127 controls the stiffness of the stiffness variable portion 51 at the bent parts 201a and 201b to a substantially straight stiffness until the radius of curvature at the time T2 exceeds the threshold value.

In the first embodiment, the parts at which the radius of curvature is below the threshold value are constantly determined as bent parts 201a and 201b, and are changed in stiffness. However, in the present modification, since the bent parts 201a and 201b are determined on the basis of the change amount of the radius of curvature in a desired period of time, it is possible to reduce the load on the controller 127 that controls the stiffness of the stiffness variable portions 51.

The radius of curvature is used in the present modification; however, the curvature may be used instead. The curvature is the reciprocal of the radius of curvature. Accordingly, the main determiner 125 determines, on the basis of the threshold value set in advance and the change amount of the curvature in the desired period of time, that the parts at which the curvature after passage of the desired period of time exceeds the threshold value are bent parts 201a and 201b. The controller 127 controls the stiffness of the stiffness variable portions 51 until the curvature falls below the threshold value.

Second Modification

Figure 5A:
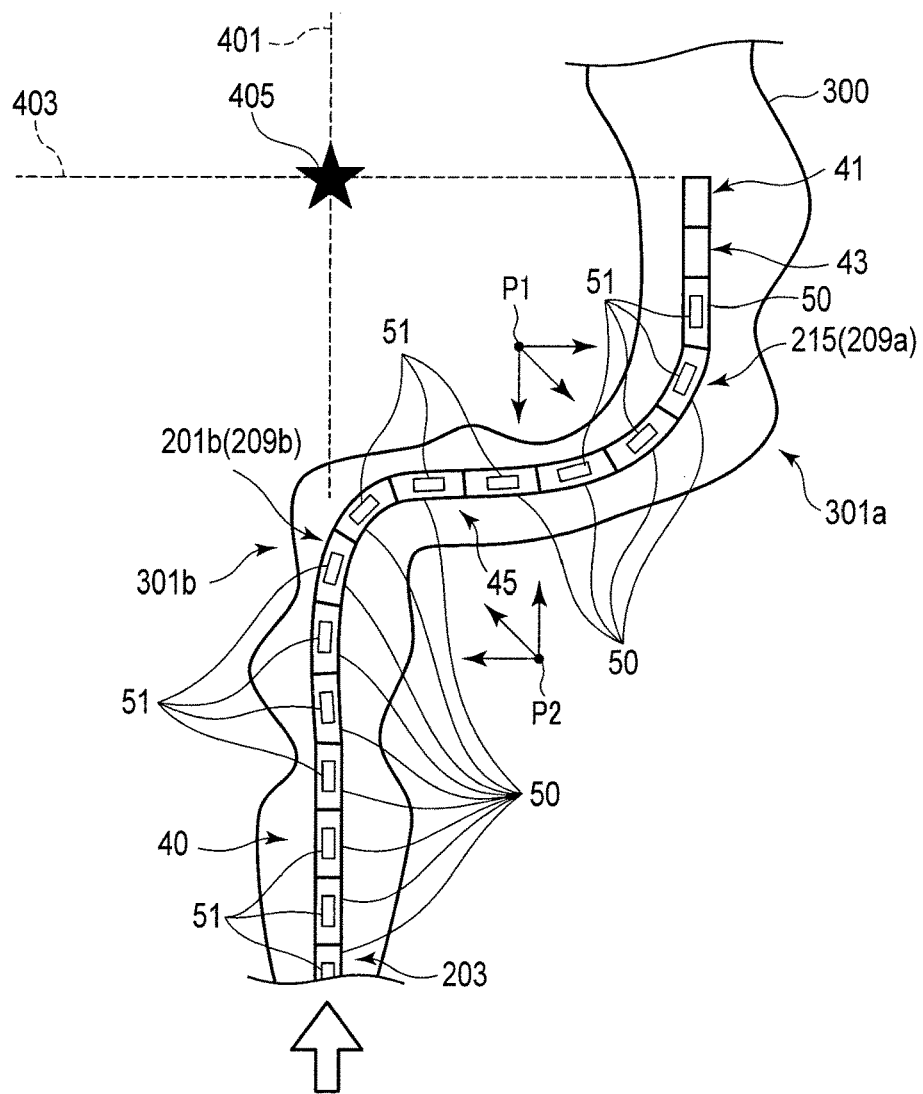
FIG. 5A is a diagram showing a state in which the insertion section is passing through the bent portion of the tube, according to a second modification of the first embodiment.
Figure 5B:
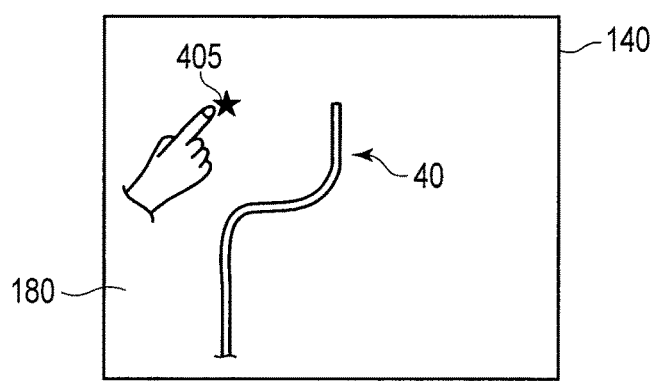
FIG. 5B is a diagram showing an input operation of an origin point from an input portion arranged in the display apparatus, according to the second modification of the first embodiment.

A second modification of the first embodiment will be explained with reference to FIGS. 5A, 5B, and 5C. In the present modification, only the features different from those of the first embodiment will be described.

Bending information of the present modification represents a radius of curvature that is a magnitude of a bend of an insertion section 40. Here, as shown in FIG. 5A, the intersection of a first extension line 401 of a central axis of a part of the insertion section 40 located at an entrance of a tube 300 of a subject and a second extension line 403 of an orthogonal axis that is orthogonal to the central axis of a distal end portion of the insertion section 40 inserted into the tube 300 of the subject is defined as an origin point 405. In the present modification as well, the display apparatus 140 displays the current state information of the insertion section 40 inside of the tube 300 on the basis of the detection result of the detection unit 60, as shown in FIG. 5B. The insertion apparatus 10 includes an input portion 180 that is arranged in the display apparatus 140, and inputs the origin point 405 on the basis of the state information of the insertion section 40 displayed on the display apparatus 140. The input portion 180 is, for example, a touch panel arranged on the display apparatus 140. Accordingly, the origin point 405 is input by the operator's operation on the input portion 180, in a state in which the operator is visually observing the current state information of the insertion section 40 inside of the tube 300 displayed on the display apparatus 140. The positional information on the input origin point 405 is output to the main determiner 125. Thus, the origin point 405 is input to the main determiner 125 on the basis of the shape information of the insertion section 40.

Figure 5C:
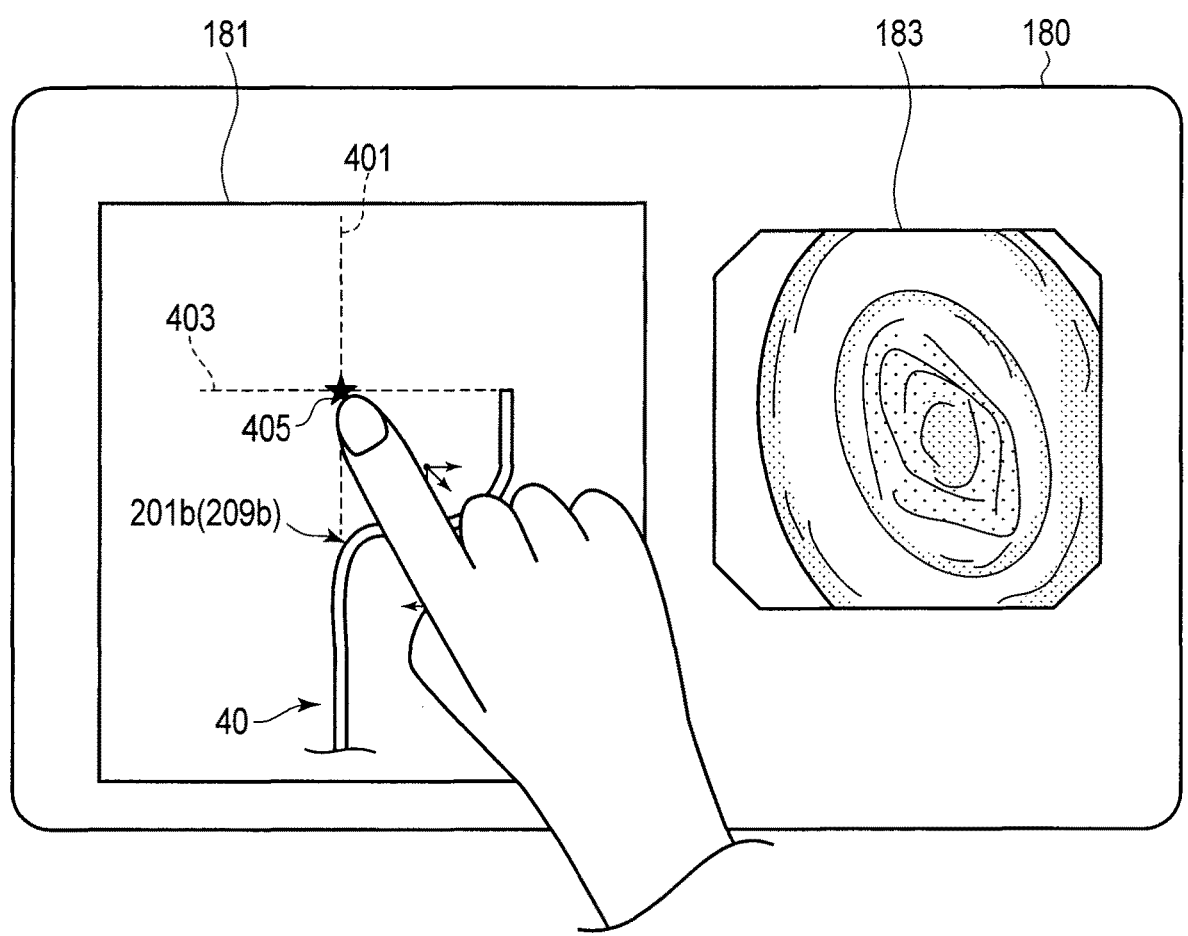
FIG. 5C is a diagram showing an input operation of an origin point from an input portion provided separately from the display apparatus, according to the second modification of the first embodiment.

The input portion 180 may be a portable terminal such as a tablet provided separately from the display apparatus 140, as shown in FIG. 5C. In this case, the input portion 180 includes a first display (first display portion) 181 and a second display (second display portion) 183, which synchronously display display information displayed on the display apparatus 140. The first display 181 displays the current state information of the insertion section 40 inside of the tube 300, for example. The second display 183 displays an image taken by, for example, an imager. The input portion 180 is connected to the insertion control apparatus 120 by wireless, for example. The input portion 180 is, for example, a general input device, and may be, for example, a pointing device such as a keyboard, a mouse, etc.

The main determiner 125 compares the threshold value set in advance and the radius of curvature, and determines that the parts at which the radius of curvature is below the threshold value are the bent parts 201a and 201b, as in the first embodiment. Furthermore, the main determiner 125 determines that the part at which the radius of curvature has a central position P2 (see FIG. 5A), that is located on the side opposite to the origin point 405 with the insertion section 40 interposed therebetween, is the bent part 201b generated by buckling. For example, when the insertion section 40 passes through the sigmoid colon, as shown in FIG. 5A, the bent part 201b in the sigmoid colon is a part where buckling may occur, and needs to be increased in bending stiffness. In this case, since the central position P2 is located on the side opposite to the origin point 405 with the insertion section 40 interposed therebetween, the main determiner 125 determines that the passing part 209b that passes through the sigmoid colon is the bent part 201b.

The main determiner 125 determines that the part on the side of the origin point 405, e.g., the part at which the radius of curvature has a central position P1 between the origin point 405 and the insertion section 40, is the bending part 215 generated in the course of insertion. For example, when the insertion section 40 passes through the descending colon located between the sigmoid colon and the transverse colon, the bending part 215 is the part at which the insertion section 40 is bent toward the inside of the lumen in the course of insertion. Accordingly, the bending stiffness of the bending part 215 does not need to be increased. In this case, the central position P1 is located on the side of the origin point 405, e.g., between the origin point 405 and the insertion section 40, and the main determiner 125 determines that the passing part 209a that passes through the descending colon is the bending part 215.

The controller 127 controls only the stiffness of the stiffness variable portion 51 in the bent part 201b to be a stiffness that makes the radius of curvature exceed the threshold value.

In the present modification, when the insertion section 40 is inserted from the sigmoid colon into the transverse colon, only the bending stiffness of the passing part 209b that passes through the sigmoid colon can be changed, thus eliminating the change in bending stiffness of the passing part 209a that passes through the descending colon located between the sigmoid colon and the transverse colon. It is thus possible in the present modification to prevent occurrence of buckling, and to improve insertability of the insertion section 40.

The bending information may represent the direction of the bend of the insertion section 40. In this case, the main determiner 125 determines that the periphery of the part at which the direction of the bend is toward the origin point 405 is a bent part. The controller 127 controls only the stiffness of the stiffness variable portions 51 in the bent part in such a manner that most of the directions of the bends in the bent part become the same direction.

The radius of curvature is used in the present modification; however, the curvature may be used instead. The curvature is the reciprocal of the radius of curvature.

Accordingly, the main determiner 125 determines that the part at which the curvature has a central position P2 (see FIG. 5A), located on the side opposite to the origin point 405 with the insertion section 40 interposed therebetween, is the bent part 201b generated by buckling. The controller 127 controls only the stiffness of the stiffness variable portion 51 in the bent part 201b to be a stiffness that makes the curvature fall below the threshold value.

Third Modification

A third modification of the first embodiment will be explained with reference to FIGS. 6A, 6B, and 6C. In the present modification, only the features different from those of the first embodiment will be described.

Figure 6B:
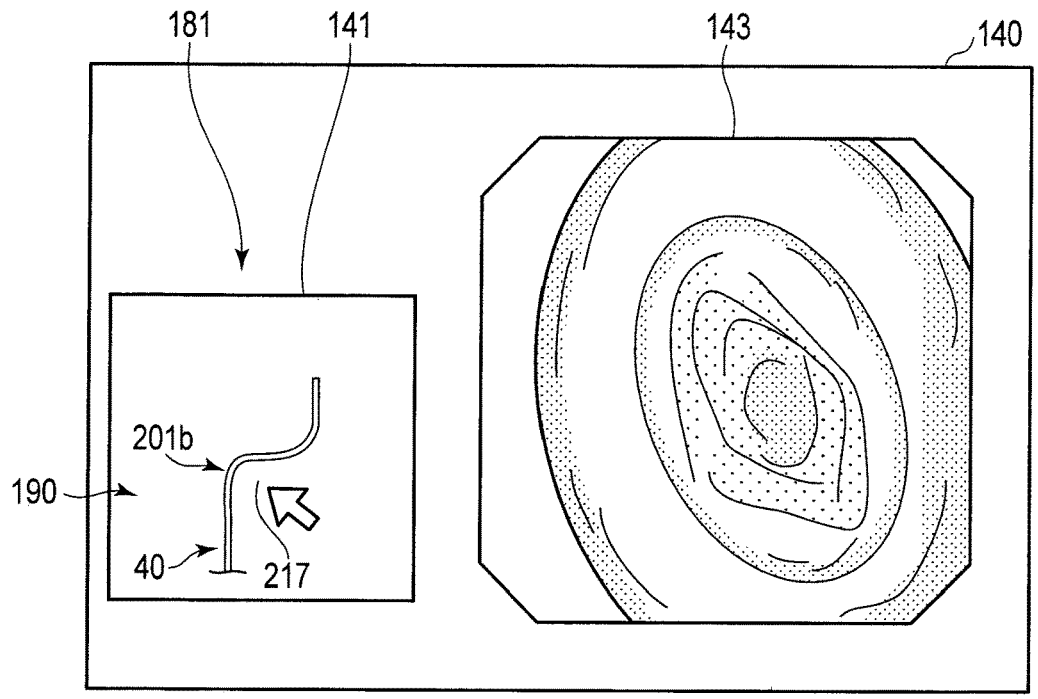
FIG. 6B is a diagram showing an example of an input operation of a designated part from the input portion arranged in the display apparatus.
Figure 6C:
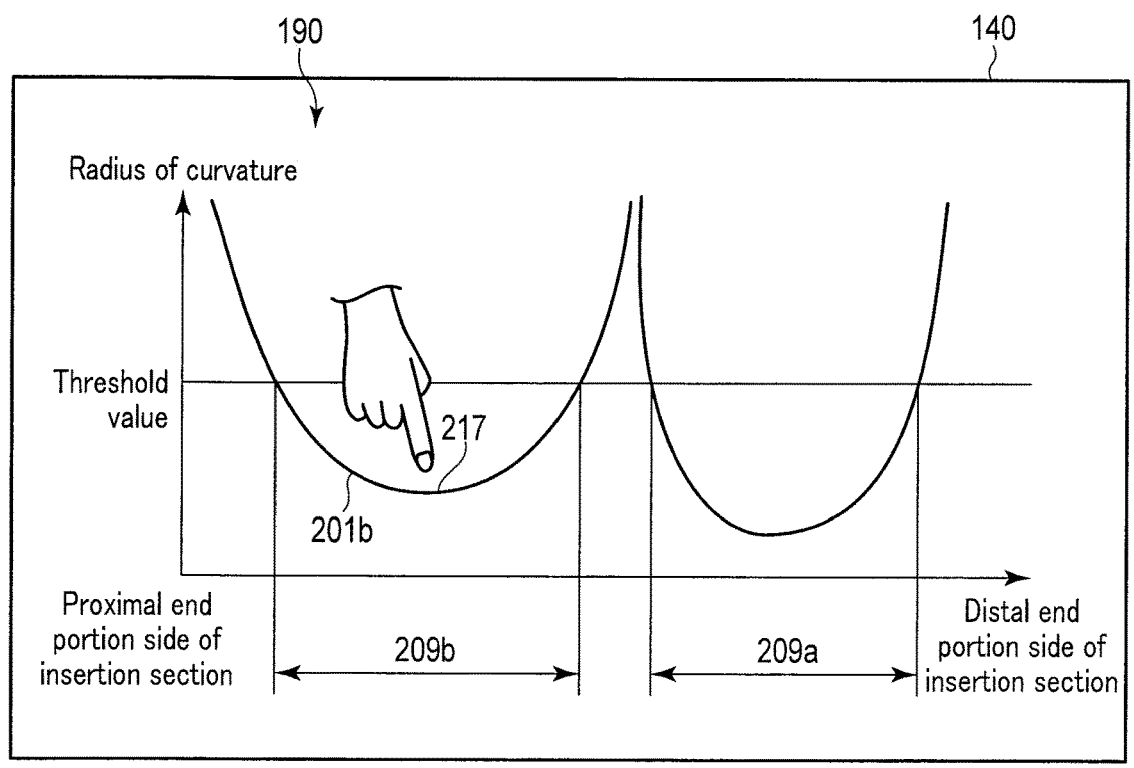
FIG. 6C is a diagram showing an example of an input operation of a designated part from the input portion arranged in the display apparatus.

In the present modification, as shown in FIG. 6B, the display apparatus 140 includes a first display 141 that displays the current state information of the insertion section 40 inside of the tube 300, and a second display 143 that displays an image taken by the imager. The display apparatus 140 may display bending information and a threshold value, as shown in FIG. 6C. The display apparatus 140 is only required to display at least one of the current state information and bending information of the insertion section 40 inside the tube 300, on the basis of the detection result of the detection unit 60 and the calculation result of the bending information calculator 123.

The insertion apparatus 10 includes an input portion 190 that inputs a designated part 217 based on at least one of the state information and bending information of the insertion section 40 displayed on the display apparatus 140. The input portion 190 is, for example, a touch panel arranged on the display apparatus 140. The input portion 190 may be a portable terminal such as a tablet provided separately from the display apparatus 140, as in the input portion 180. Alternatively, the input portion 190 is, for example, a general input device, and may be, for example, a pointing device such as a keyboard and a mouse.

The designated part 217 is input to the main determiner 125 by the operator's operation on the input portion 190, for example, in a state in which the operator is visually observing at least one of the current state information and bending information of the insertion section 40 inside of the tube 300 displayed on the display apparatus 140. The designated part 217 may be a position or a frame.

The main determiner 125 determines whether or not the designated part 217 input from the input portion 180 is the bent part 201b, on the basis of one of the state information and the bending information displayed on the display apparatus 140. The main determiner 125 compares the radius of curvature of the designated part 217 and the threshold value, and determines that the designated part 217 is the bent part 201b when the radius of curvature has fallen below the threshold value.

The controller 127 performs control in a manner similar to the first embodiment.

In the present modification, the operator visually observes at least one of the state information and the bending information of the insertion section 40 displayed on the display apparatus 140, and the operator selects a bent part 201b via the designated part 217. It is thus possible to select a part at which the bending stiffness is to be changed, thus improving the insertion efficiency of the insertion section 40.

The present invention is not limited to the above-described embodiment and can be embodied in practice by modifying the structural elements without departing from the gist of the invention. In addition, various inventions can be made by suitably combining the structural elements disclosed in connection with the above embodiment.

What is claimed is:
1. A flexible tube insertion apparatus comprising:
an insertion section divided into a plurality of segments arranged in a column shape along a longitudinal axis direction of the insertion section, the insertion section being configured to be inserted into a subject;
at least one stiffness variable material provided in each of the plurality of segments, the stiffness variable material comprising a shape memory alloy configured to change a bending stiffness of the insertion section in a corresponding one of the plurality of segments in accordance with a value of an applied electric force; and
one or more processors comprising hardware, the one or more processors being configured to:
receive state information of the insertion section including at least shape information of the insertion section;

calculate, based on the received shape information of the insertion section, bending information of the insertion section including information on a magnitude of a bend of the insertion section, the information on the magnitude of the bend includes information on a radius of curvature;

determine, based on a comparison of the calculated information on the radius of curvature of the insertion section and a threshold value set in advance for the magnitude of the bend, whether or not a bent part is present in the insertion section when the radius of curvature has fallen below the threshold value, and a position of the bent part in the insertion section when the bent part is present; and when the bent part is determined to be present in the insertion section, control the electric force applied to the at least one stiffness variable material to change a stiffness of the at least one stiffness variable material provided in each segment of the plurality of segments corresponding to the bent part;

wherein an intersection of a first extension line of a central axis of a part of the insertion section located at an entrance of the subject and a second extension line of an orthogonal axis that is orthogonal to a central axis of a distal end portion of the insertion section inserted into the subject is defined as an origin point, and the one or more processors are configured to:
determine that a part at which the radius of curvature has a central position located on a side opposite to the origin point with the insertion section interposed therebetween is the bent part, and control the stiffness of the at least one stiffness variable material to be a stiffness that makes the radius of curvature exceed the threshold value for the radius of curvature.

2. The flexible tube insertion apparatus according to claim 1, further comprising a display that displays the state information of the insertion section;
wherein the one or more processors are configured to receive an input of the origin point.

3. The flexible tube insertion apparatus according to claim 1, further comprising a display that displays at least one of the state information and the bending information of the insertion section,
wherein the one or more processors are configured to determine whether or not a designated part input based on one of the state information and the bending information displayed on the display apparatus is the bent part.

4. The flexible tube insertion apparatus according to claim 3, wherein the one or more processors are configured to receive an input of the designated part.

5. The flexible tube insertion apparatus according to claim 1, wherein the one or more processors are configured to perform control to decrease the stiffness of the stiffness variable material that is located in the segment having passed through a desired part of the subject and controlled to increase the stiffness, based on the shape information of the insertion section.

6. The flexible tube insertion apparatus according to claim 1, wherein the one or more processors are configured to perform control to increase the stiffness of the stiffness variable material that is located in the segment located ahead of or behind the segment arranged in the bent part.

7. The flexible tube insertion apparatus according to claim 1, wherein the one or more processors are configured to receive a control start instruction to start control of the application of the electric force to the at least one stiffness variable material.

8. A flexible tube insertion apparatus comprising:
an insertion section divided into a plurality of segments arranged in a column shape along a longitudinal axis direction of the insertion section, the insertion section being configured to be inserted into a subject;

at least one stiffness variable material provided in each of the plurality of segments, the stiffness variable material being configured to change a bending stiffness of the insertion section in a corresponding one of the plurality of segments; and one or more processors comprising hardware, the one or more processor being configured to:
receive state information of the insertion section including at least shape information of the insertion section;

calculate, based on the received shape information of the insertion section, bending information of the insertion section including information on a magnitude of a bend of the insertion section, the information on the magnitude of the bend includes information on a radius of curvature;

determine, based on a comparison of the calculated information on the radius of curvature of the insertion section and a threshold value set in advance for the magnitude of the bend, whether or not a bent part is present in the insertion section when the radius of curvature has fallen below the threshold value, and a position of the bent part in the insertion section when the bent part is present; and when the bent part is determined to be present in the insertion section, control the at least one stiffness variable material to change a stiffness of the at least one stiffness variable material provided in each segment of the plurality of segments corresponding to the bent part;

wherein an intersection of a first extension line of a central axis of a part of the insertion section located at an entrance of the subject and a second extension line of an orthogonal axis that is orthogonal to a central axis of a distal end portion of the insertion section inserted into the subject is defined as an origin point, and the one or more processors are configured to:
determine that a part at which the radius of curvature has a central position located on a side opposite to the origin point with the insertion section interposed therebetween is the bent part, and control the stiffness of the stiffness variable material to be a stiffness that makes the radius of curvature exceed the threshold value for the radius of curvature.

* * * * *